United States Patent
Li et al.

(10) Patent No.: US 10,280,365 B2
(45) Date of Patent: May 7, 2019

(54) LIGHT EMITTING MATERIAL, MANUFACTURE METHOD THEREOF AND ORGANIC LIGHT EMITTING DIODE USING THE LIGHT EMITTING MATERIAL

(71) Applicant: Shenzhen China Star Optoelectronics Technology Co., Ltd., Shenzhen (CN)

(72) Inventors: Xianjie Li, Shenzhen (CN); Yuanchun Wu, Shenzhen (CN); Shijian Su, Shenzhen (CN); Yunchuan Li, Shenzhen (CN)

(73) Assignee: SHENZHEN CHINA STAR OPTOELECTRONICS TECHNOLOGY CO., LTD., Shenzhen, Guangdong (CN)

( * ) Notice: Subject to any disclaimer, the term of this patent is extended or adjusted under 35 U.S.C. 154(b) by 205 days.

(21) Appl. No.: 15/122,410

(22) PCT Filed: Aug. 17, 2016

(86) PCT No.: PCT/CN2016/095615
§ 371 (c)(1),
(2) Date: Aug. 30, 2016

(87) PCT Pub. No.: WO2018/014408
PCT Pub. Date: Jan. 25, 2018

(65) Prior Publication Data
US 2018/0201832 A1 Jul. 19, 2018

(30) Foreign Application Priority Data
Jul. 20, 2016 (CN) .......................... 2016 1 0579646

(51) Int. Cl.
| | | |
|---|---|---|
| C07D 409/14 | (2006.01) |
| H01L 51/00 | (2006.01) |
| C09K 11/06 | (2006.01) |
| C07D 417/14 | (2006.01) |
| C07D 335/16 | (2006.01) |
| C07D 339/08 | (2006.01) |
| H01L 51/50 | (2006.01) |
| H01L 51/52 | (2006.01) |
| H01L 51/56 | (2006.01) |

(52) U.S. Cl.
CPC ............. *C09K 11/06* (2013.01); *C07D 335/16* (2013.01); *C07D 339/08* (2013.01); *C07D 409/14* (2013.01); *C07D 417/14* (2013.01); *H01L 51/0074* (2013.01); *C09K 2211/1037* (2013.01); *H01L 51/5012* (2013.01); *H01L 51/5056* (2013.01); *H01L 51/5072* (2013.01); *H01L 51/5092* (2013.01); *H01L 51/5206* (2013.01); *H01L 51/5221* (2013.01); *H01L 51/56* (2013.01)

(58) Field of Classification Search
CPC .................................................. C07D 409/14
See application file for complete search history.

(56) References Cited

FOREIGN PATENT DOCUMENTS

| CN | 103189368 A | 7/2013 |
|---|---|---|
| CN | 104761547 A | 7/2015 |

*Primary Examiner* — Brian E McDowell
(74) *Attorney, Agent, or Firm* — Leong C. Lei

(57) ABSTRACT

A light emitting material of the constitutional formula

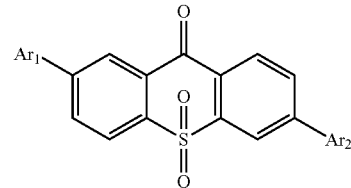

is provided. The structure is unitary, and the formula weight is determined, and the better solubility and film formation are provided, and the thin film status is stable; it possesses a very high decomposition temperature and a lower sublimation temperature, and is easy to sublime to be light emitting material of high purity, and can be applied for small molecule organic light emitting diode. In a manufacture method of the light emitting material, p-bromothiophenol and 4-Bromo-2-fluorobenzonitrile are employed as starting materials, and the intermediate of the light emitting material is obtained with a series of simple reactions, and finally, the light emitting material is obtained with Ullmann reaction or Suzuki reaction, and the steps are simple and the production is high.

6 Claims, 2 Drawing Sheets

LIGHT EMITTING MATERIAL, MANUFACTURE METHOD THEREOF AND ORGANIC LIGHT EMITTING DIODE USING THE LIGHT EMITTING MATERIAL

FIELD OF THE INVENTION

The present invention relates to a display technology field, and more particularly to a light emitting material, a manufacture method thereof and an organic light emitting diode using the light emitting material.

BACKGROUND OF THE INVENTION

The OLED (Organic Light-Emitting Diode) display, which is also named as the Organic light emitting display, is a new flat panel display device. Because it possesses advantages of simple manufacture process, low cost, low power consumption, high light emitting brightness, wide operating temperature range, thin volume, fast response speed, and being easy to achieve the color display and the large screen display, and being easy to achieve the match with the integrated circuit driver, and being easy to achieve the flexible display. Therefore, it has the broad application prospects.

The OLED display utilizes the organic light emitting diode for light emission. Thus, it is extremely important to improve the efficiency and lifetime of the organic light emitting diode. Now, the organic light emitting diode has already made considerable progress. With the fluorescence phosphorescence hybrid, the white light element with the simple structure and high efficiency can be obtained. The efficiency of such fluorescence phosphorescence hybrid element significantly relies on the efficiency of the fluorescence. Therefore, it still has vital significant meaning to develop the high efficiency fluorescence material.

In comparison with polymer, the small molecule light emitting molecule has the simple steps, the stable structure and can be purified, and then the higher element efficiency can be obtained for the possible commercial application. The method of manufacturing multiple layer element by implementing evaporation or solution process with small molecule has already drawn the great attention and the great progress has been made. However, the traditional organic fluorescence material only can utilize 25% of singlet excitons. Thus, there is extreme big restriction to the efficiency of the element. Recently, the Japanese Adachi research group utilizes the thermally activated delayed fluorescence mechanism to make the exciton availability of all organic material reach up to 100%, and the organic fluorescence element efficiency progresses significantly. Nevertheless, there is few for such kind of materials. Therefore, the type expansion for such kind of material has the significant meaning for the application in the future. For now, the organic small molecule light emitting material of simple structure, and possessing well performance and satisfying the commercialization requirement is still so limited. It is still profound to develop the light emitting material of low cost and excellent efficiency.

SUMMARY OF THE INVENTION

An objective of the present invention is to provide a light emitting material, in which the structure is unitary, and the formula weight is determined, and the better solubility and film formation are provided to be applied for small molecule organic light emitting diode.

Another objective of the present invention is to provide a manufacture method of the light emitting material, in which the steps are simple, and the production is high.

Another objective of the present invention is to provide an organic light emitting diode, in which the light emitting layer comprises the aforesaid light emitting material that has higher light emission efficiency and stability.

For realizing the aforesaid objectives, the present invention first provides a light emitting material, in which a constitutional formula is

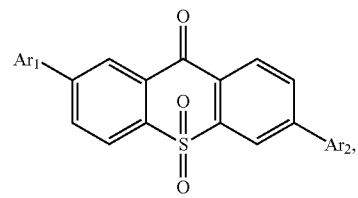

wherein $Ar_1$ and $Ar_2$ are respectively selected from aromatic amine groups shown in formula (1), formula (2), formula (3), formula (4), formula (5), formula (6), formula (7);

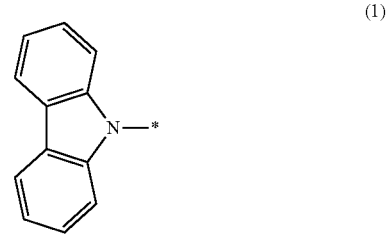

(1)

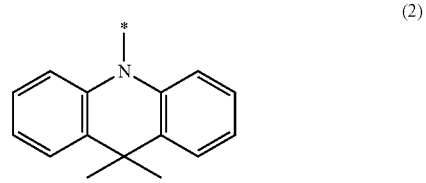

(2)

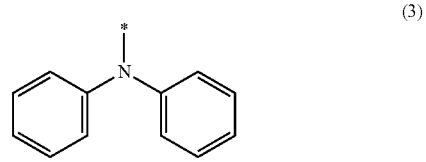

(3)

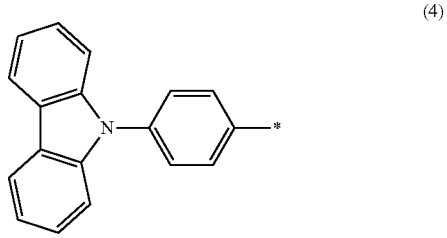

(4)

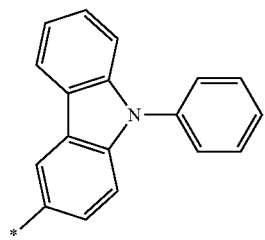
(5)
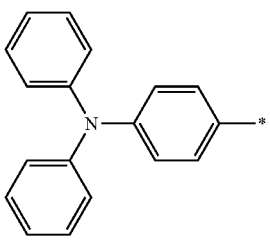
(6)
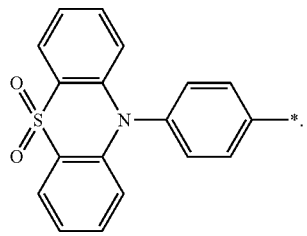
(7)
Ar₁ and Ar₂ are the same.
The light emitting material comprises one or more of following compounds:
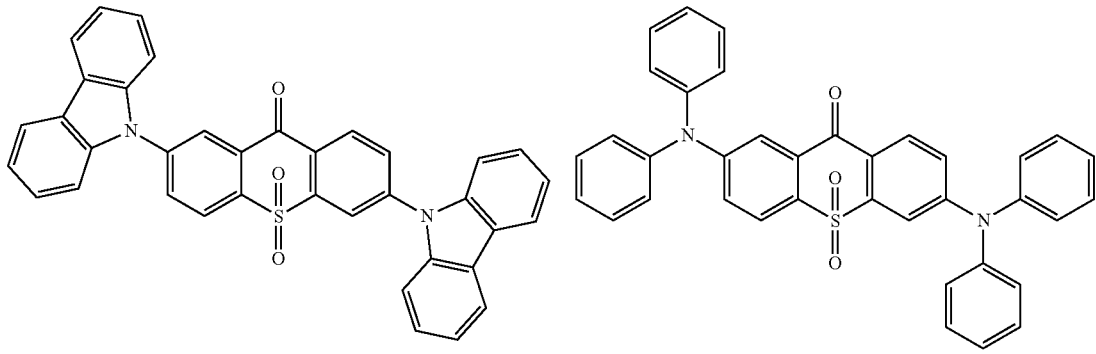
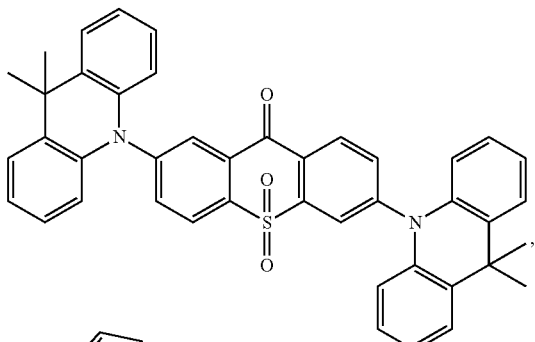
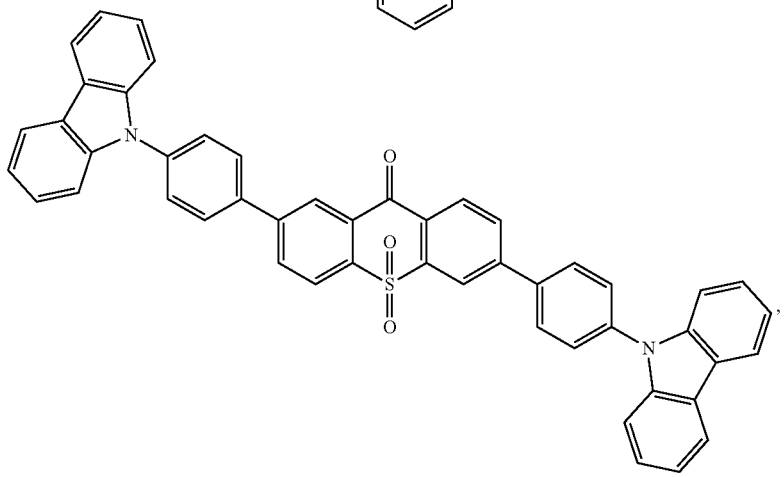

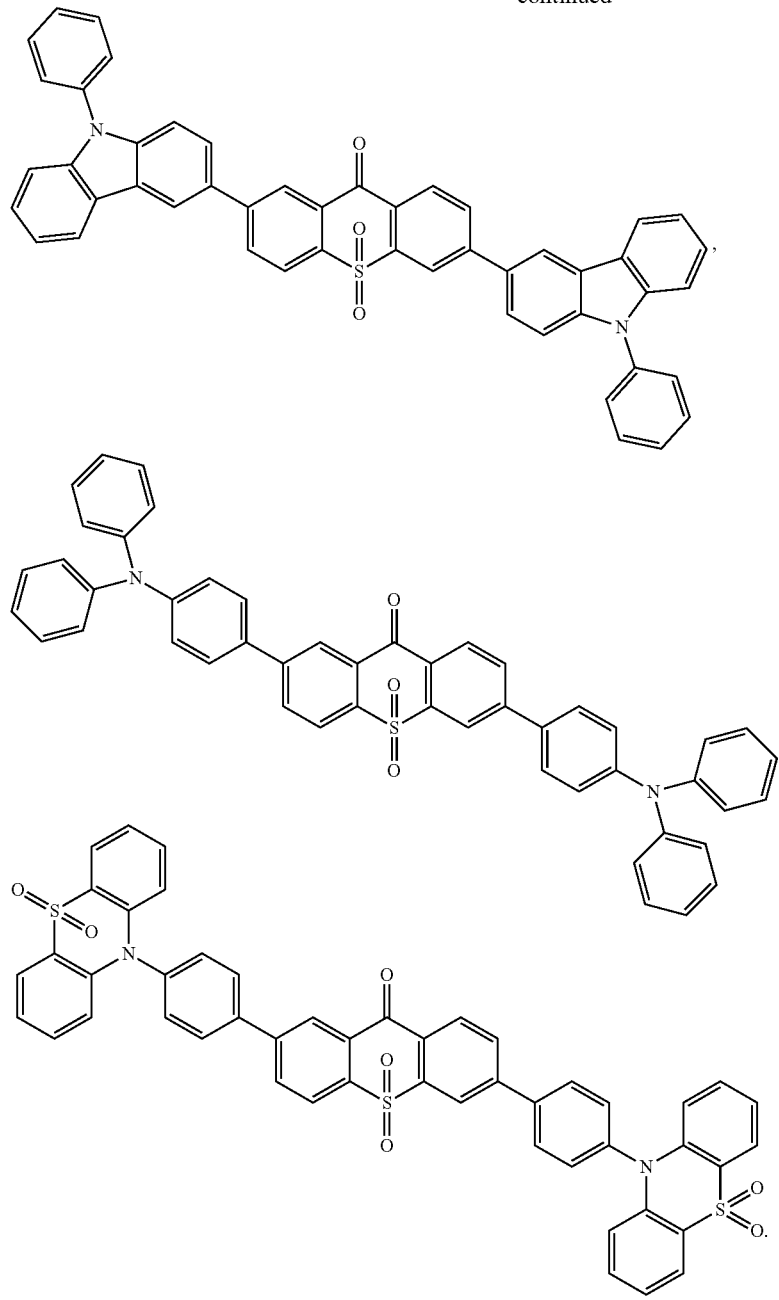
The present invention further provides a manufacture method of light emitting material, comprising steps of:
step 1, manufacturing an intermediate
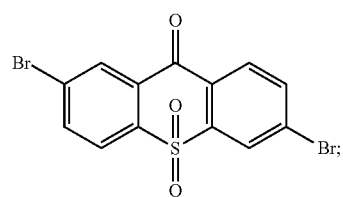
step 2, obtaining light emitting material with Ullmann reaction or Suzuki reaction of the intermediate
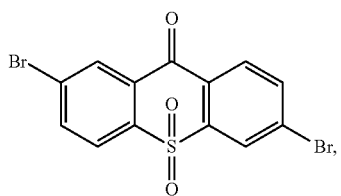
and an aromatic amine compound, in which a constitutional formula of the light emitting material is

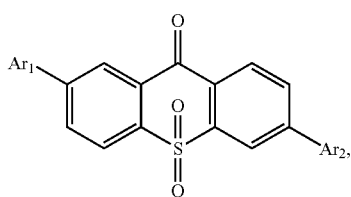
wherein $Ar_1$ and $Ar_2$ are respectively selected from aromatic amine groups shown in formula (1), formula (2), formula (3), formula (4), formula (5), formula (6), formula (7);
(1)
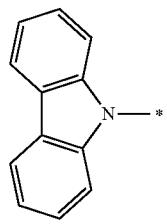
(2)
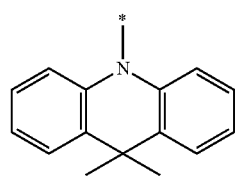
(3)
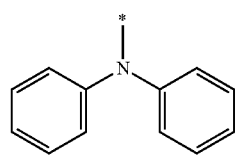
(4)
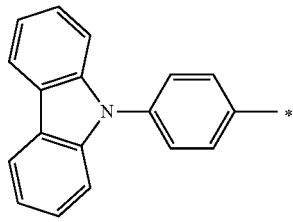
(5)
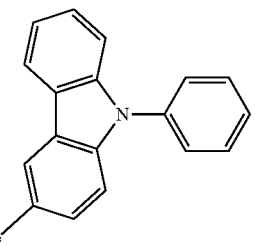
(6)
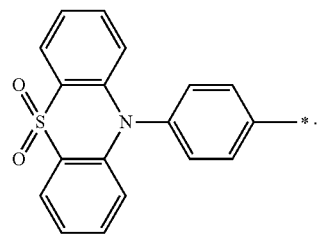
(7)
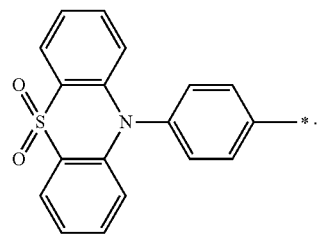
$Ar_1$ and $Ar_2$ are the same.
The light emitting material comprises one or more of following compounds:
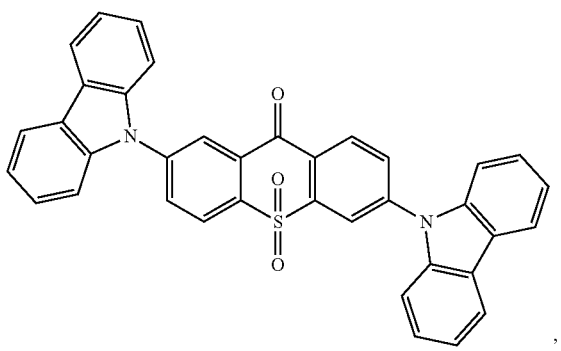
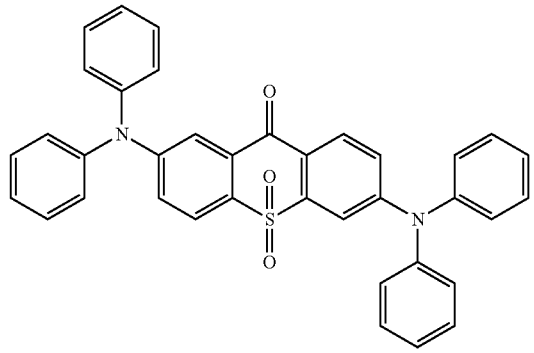

-continued
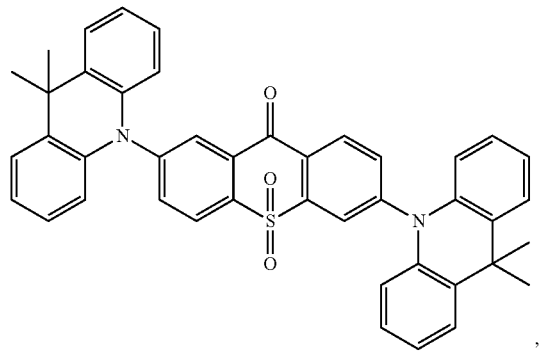
,
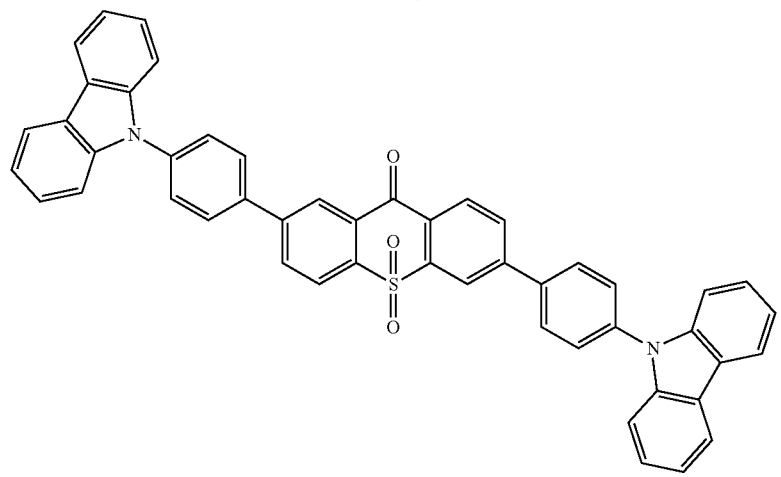
,
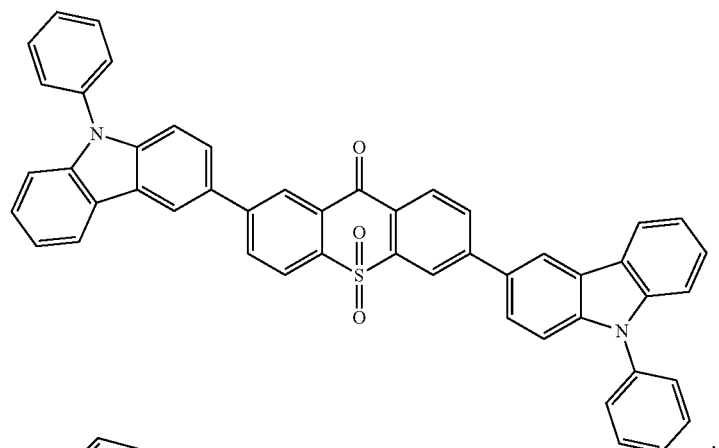
,
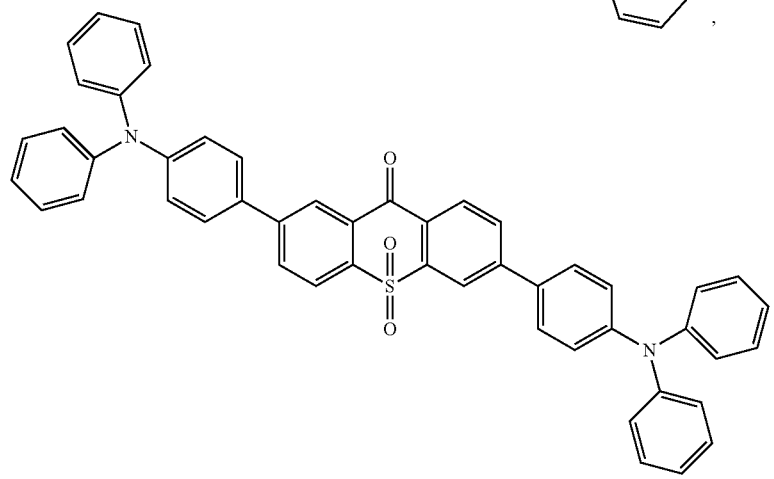

-continued

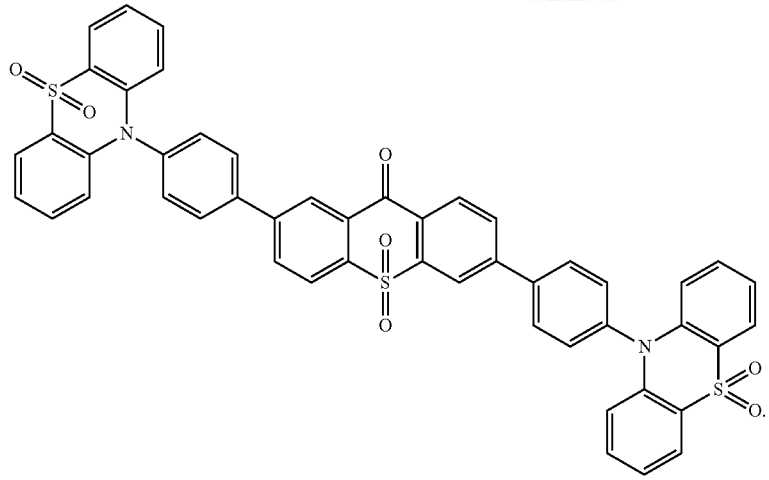

The step 1 comprises:
step 11, obtaining

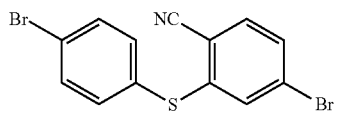 [SMILES: N#Cc1ccc(Br)cc1Sc1ccc(Br)cc1]
(25)

with a reaction of p-bromothiophenol and 4-Bromo-2-fluorobenzonitrile;
step 12, hydrolyzing

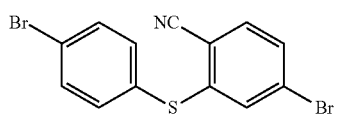 [SMILES: N#Cc1ccc(Br)cc1Sc1ccc(Br)cc1]

in an alkaline condition, and acidizing the same to obtain

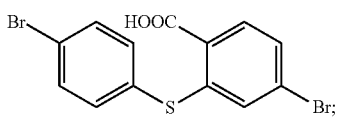

step 13, generating dehydration condensation reaction to

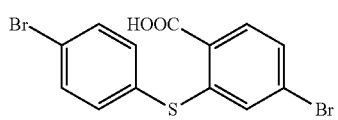 [SMILES: O=C(O)c1ccc(Br)cc1Sc1ccc(Br)cc1]

to obtain

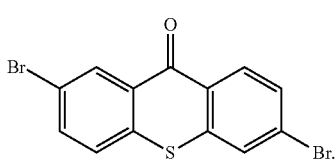 [SMILES: O=c1c2ccc(Br)cc2sc2ccc(Br)cc12]

step 14, obtaining the intermediate

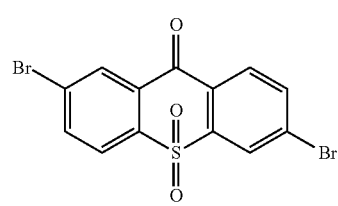

with a reaction of

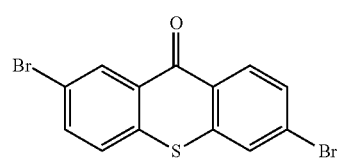 [SMILES: O=c1c2ccc(Br)cc2sc2ccc(Br)cc12]

and hydrogen peroxide.

The present invention provides an organic light emitting diode, comprising a substrate, and an anode, a Hole Injection Layer, a Hole Transporting Layer, a light emitting layer, an Electron Transport Layer, an Electron Injection Layer and a cathode stacking up on the substrate from bottom to top in order;

the light emitting layer comprises light emitting material, in which a constitutional formula is

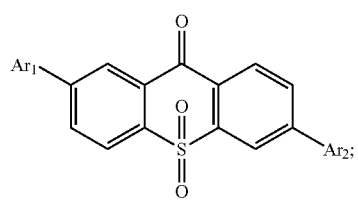

wherein $Ar_1$ and $Ar_2$ are respectively selected from aromatic amine groups shown in formula (1), formula (2), formula (3), formula (4), formula (5), formula (6), formula (7);

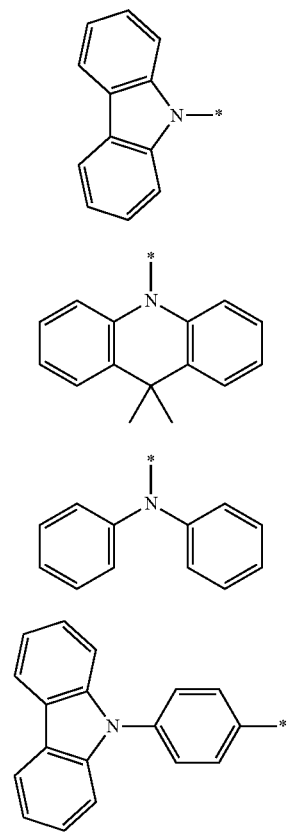
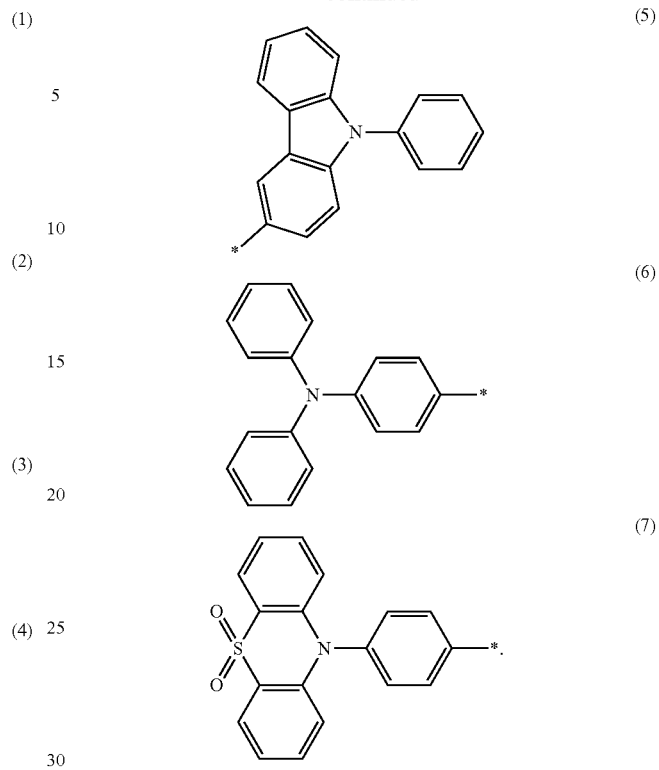
Ar₁ and Ar₂ are the same.
The light emitting material comprises one or more of following compounds:
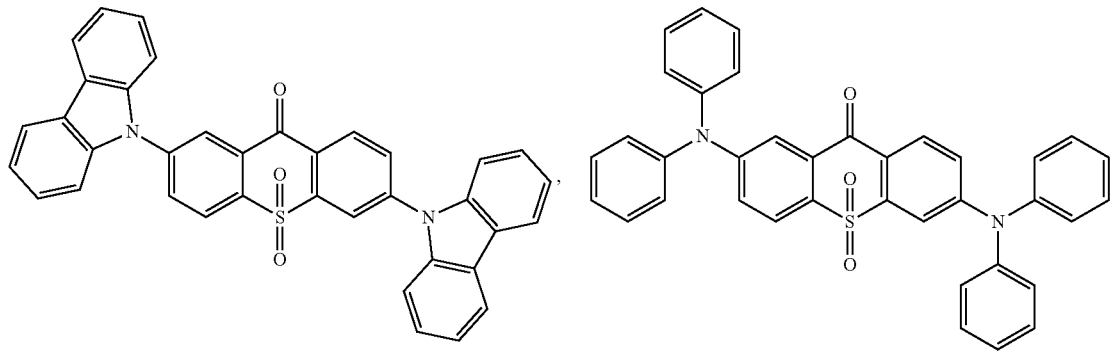
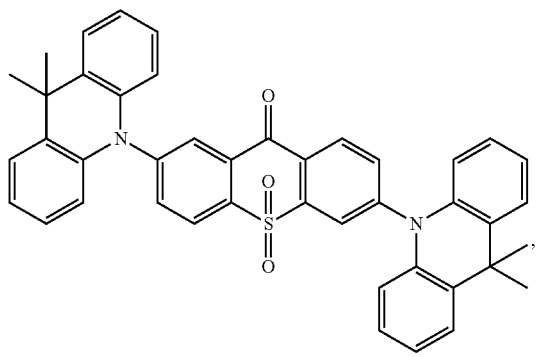

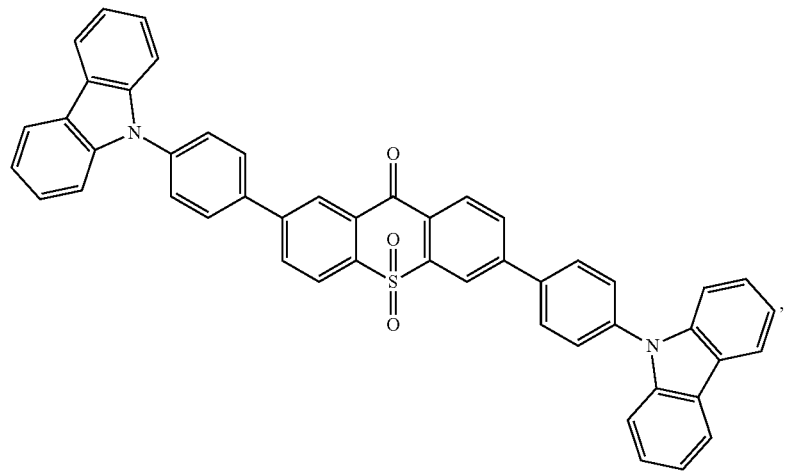
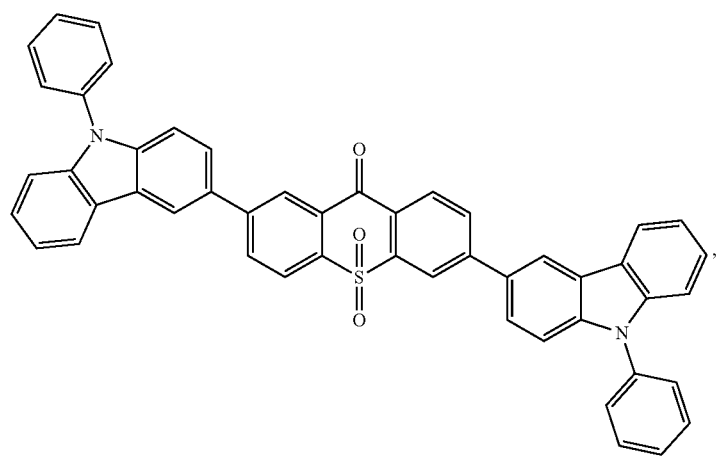
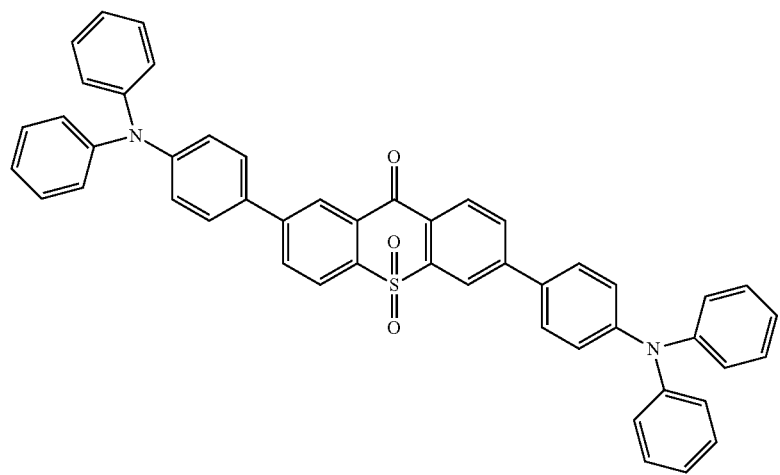

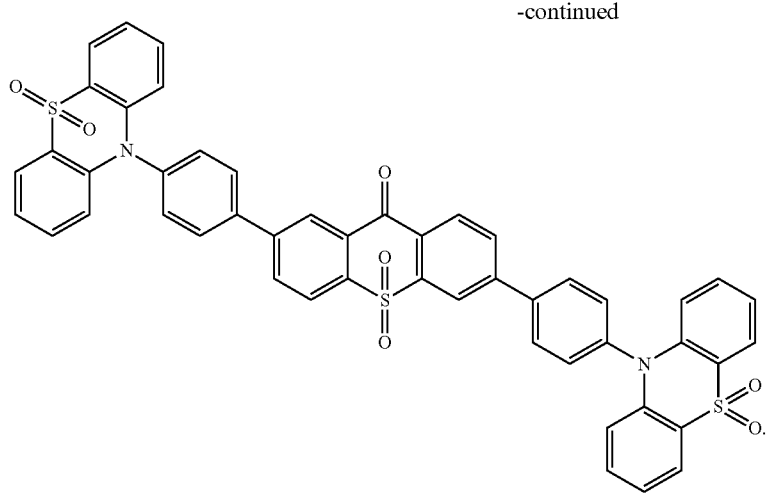

The benefits of the present invention are: the present invention provides a light emitting material, in which the structure is unitary, and the formula weight is determined, and the better solubility and film formation are provided, and the thin film status is stable; it possesses a very high decomposition temperature and a lower sublimation temperature, and is easy to sublime to be light emitting material of high purity, and can be applied for small molecule organic light emitting diode; by changing the aromatic amine group, which is connected, the physical property can be improved in advance to promote the performance of the photoelectric element of the light emitting material. The present invention provides a manufacture method of the light emitting material. p-bromothiophenol and 4-Bromo-2-fluorobenzonitrile are employed to be starting materials, and the intermediate of the light emitting material is obtained with a series of simple reactions, and finally, the light emitting material is obtained with Ullmann reaction or Suzuki reaction, and the steps are simple and the production is high. The present invention provides an organic light emitting diode, in which the light emitting layer comprises the aforesaid light emitting material that has higher light emission efficiency and stability.

In order to better understand the characteristics and technical aspect of the invention, please refer to the following detailed description of the present invention is concerned with the diagrams, however, provide reference to the accompanying drawings and description only and is not intended to be limiting of the invention.

BRIEF DESCRIPTION OF THE DRAWINGS

The technical solution and the beneficial effects of the present invention are best understood from the following detailed description with reference to the accompanying figures and embodiments.

In drawings.

DETAILED DESCRIPTION OF PREFERRED EMBODIMENTS

For better explaining the technical solution and the effect of the present invention, the present invention will be further described in detail with the accompanying drawings and the specific embodiments.

The present invention first provides a light emitting material, in which a constitutional formula is

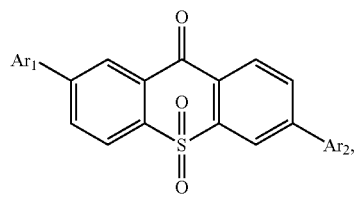

wherein $Ar_1$ and $Ar_2$ are respectively selected from aromatic amine groups shown in formula (1), formula (2), formula (3), formula (4), formula (5), formula (6), formula (7);

(1)

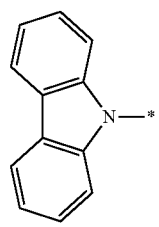

(2)

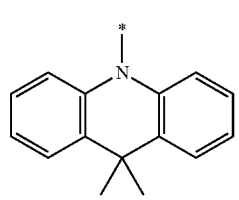

(3)

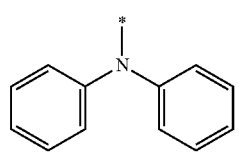

(4)
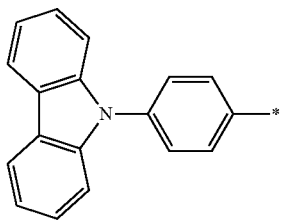
(5)
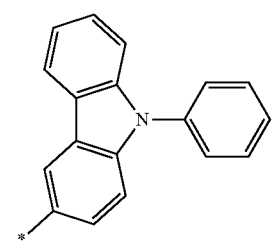
(6)
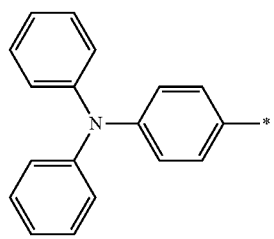
(7)
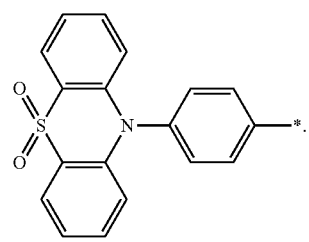
Preferably, $Ar_1$ and $Ar_2$ are the same.
Specifically, the light emitting material comprises one or more of following compounds:
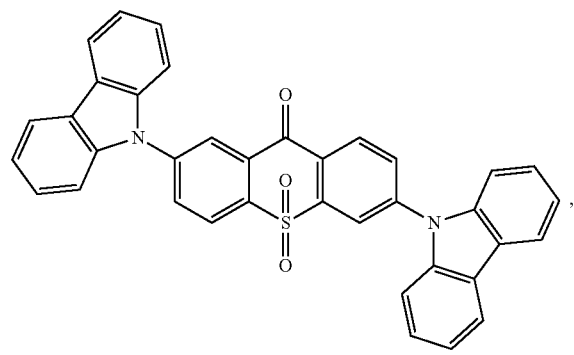,
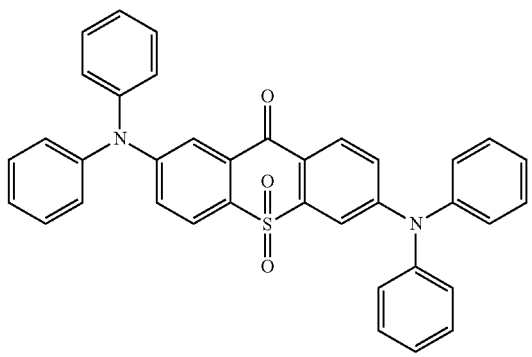
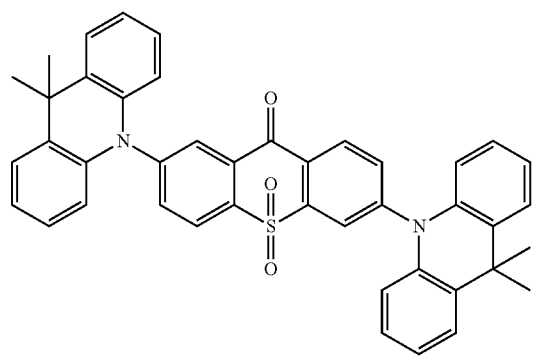,

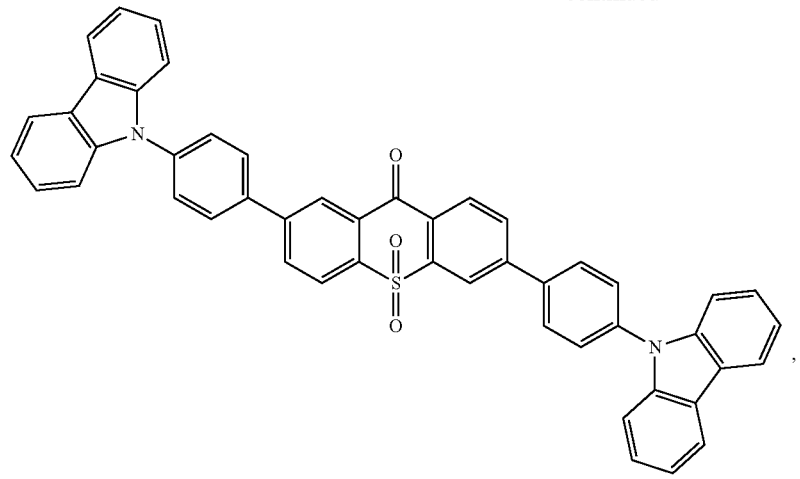
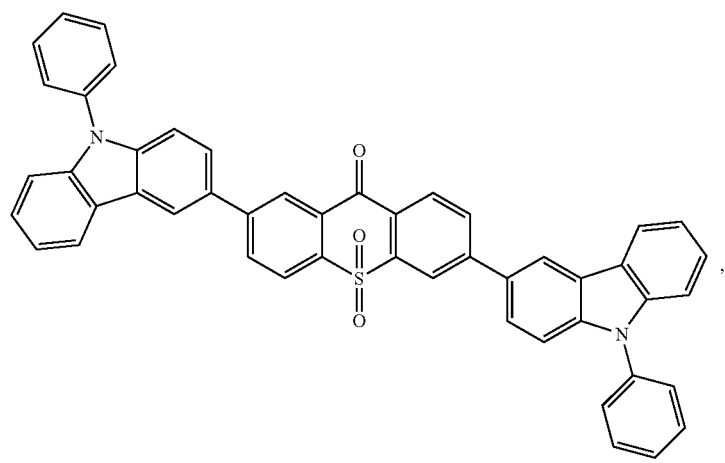
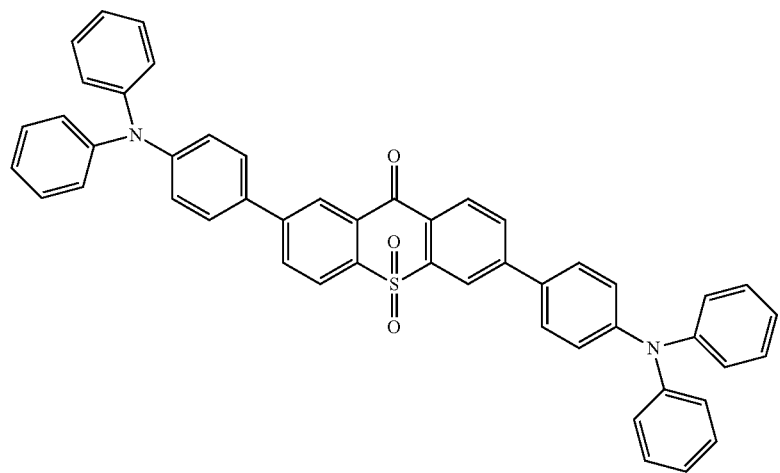

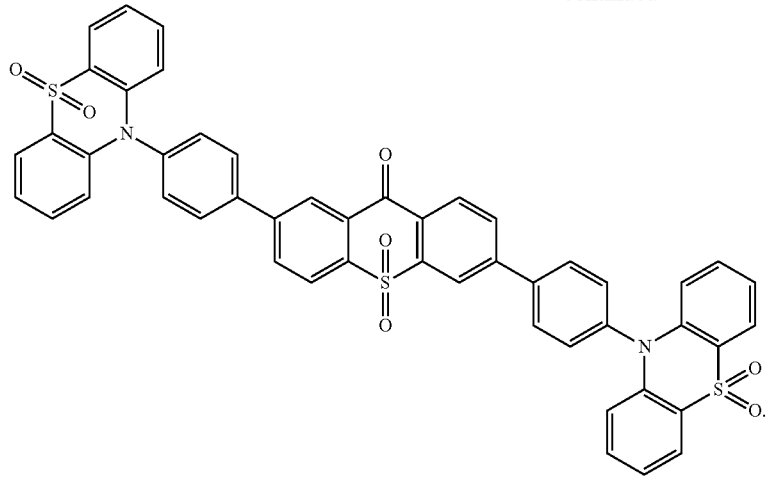

In the aforesaid light emitting material, the structure is unitary, and the formula weight is determined, and the better solubility and film formation are provided, and the thin film status is stable; it possesses a very high decomposition temperature and a lower sublimation temperature, and is easy to sublime to be light emitting material of high purity, and can be applied for small molecule organic light emitting diode; by changing the aromatic amine group, which is connected, the physical property can be improved in advance to promote the performance of the photoelectric element of the light emitting material.

Figure 1:
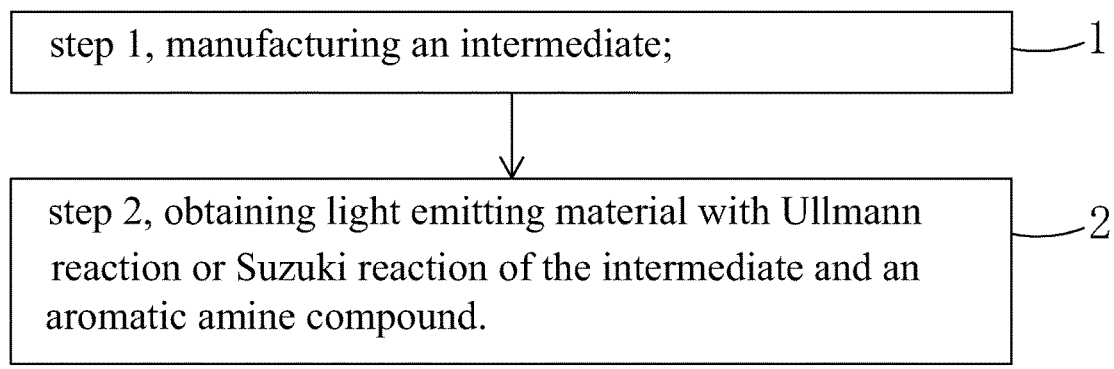
FIG. 1 is a flowchart of a manufacture method of light emitting material according to the present invention.

Please refer to FIG. 1. The present invention further provides a manufacture method of light emitting material, comprising steps of:

step 1, manufacturing an intermediate

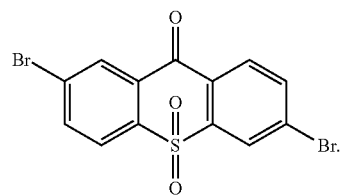

A synthetic route of the intermediate

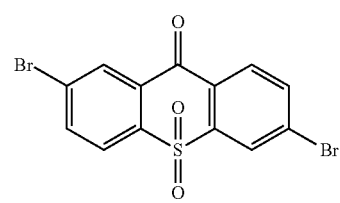

is:

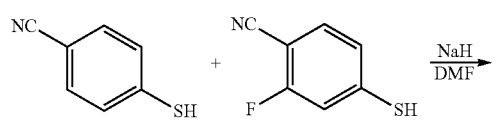

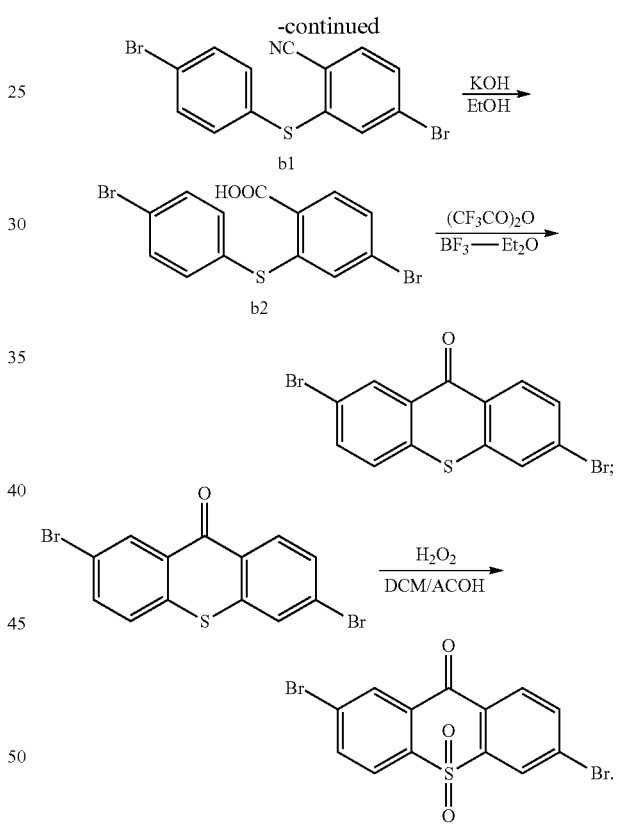

Specifically, the step 1 comprises steps of:

step 11, obtaining (b1)

with a reaction of p-bromothiophenol and 4-Bromo-2-fluorobenzonitrile.

The specific implementing steps of the step 11 are:

In 250 ml boiling flask-3-neck, 0.73 g (30 mmol) NaH is slowly added in 20 ml dry dimethylformamide (DMF) dissolved with 4.6 g (25 mmol) p-bromothiophenol, and then 20 ml dry dimethylformamide dissolved with 5 g (25 mmol) 4-Bromo-2-fluorobenzonitrile is dropped into it. Under the protection of nitrogen, 20 h heating reflux reaction is implemented, and the temperature drops to the room temperature after the reaction is completed, and then the reaction fluid is poured in 50 ml 1M NaOH solution, and extracted in dichloromethane (DCM) to be decompressed to remove the solvent, and through silicagel column, white color solid 5.2 g, i.e. the compound b1 is obtained. Molecular formula: $C_{13}H_7Br_2NS$, and MS: 366.87, and elemental analysis: C, 42.31; H, 1.91; Br, 43.30; N, 3.80; S, 8.69.

step 12, hydrolyzing

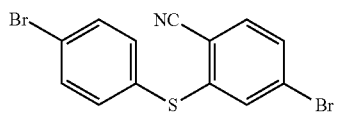 [SMILES: N#Cc1ccc(Br)cc1Sc1ccc(Br)cc1]

in an alkaline condition, and acidizing the same to obtain

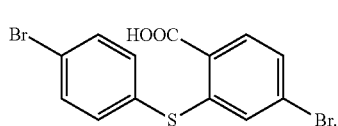

(b2)

The specific implementing steps of the step 12 are:

In 250 ml boiling flask-3-neck, 80 ml deionized water, 15 g KOH and 80 ml alcohol are added, and 5.2 g compound b1 is added in reaction bottle to reflow overnight under protection of nitrogen. After the reaction is completed, the reaction solution is cooled to the room temperature, and added in 100 ml 6M hydrochloric acid, the white solid is separated out with ice bath, and extracted and filtered, and then dried to obtain white solid 5.1 g, i.e. the compound b2. Molecular formula: $C_{13}H_8Br_2O_2S$, and MS: 385.86, and elemental analysis: C, 40.23; H, 2.08; Br, 41.18; O, 8.25; S, 8.26.

step 13, generating dehydration condensation reaction to

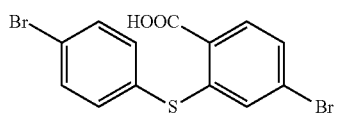 [SMILES: O=C(O)c1ccc(Br)cc1Sc1ccc(Br)cc1]

to obtain

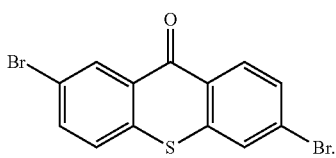 [SMILES: O=c1c2ccc(Br)cc2sc2ccc(Br)cc12]

The specific implementing steps of the step 13 are:

In 500 ml boiling flask, 2.75 g (10 mmol) compound b2 is added, and 500 ml chloroform is added to be solvent, and 3.2 g (20 mmol, 2 equ) trifluoroacetic anhydride is dropped, and stirred 10 min in the room temperature, and then 0.5 g Boron trifluoride etherate is added, and the ice bath is removed for reacting 12 h at the room temperature. After the reaction is completed, sodium sulfite saturated aqueous solution is added to quench redundant trifluoroacetic anhydride, and separated, and reduced pressure distilled to remove the solvent, and through column,

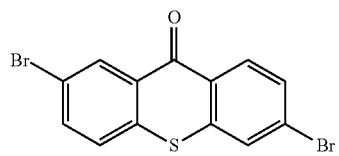 [SMILES: O=c1c2ccc(Br)cc2sc2ccc(Br)cc12]

is obtained. Molecular formula: $C_{13}H_8Br_2O_2S$; MS: 385.86; elemental analysis: C, 40.23; H, 2.08; Br, 41.18; O, 8.25; S, 8.26.

step 14, obtaining the intermediate

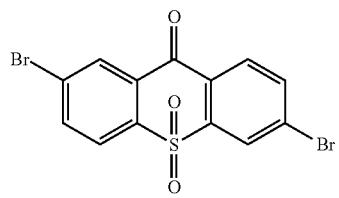

with a reaction of

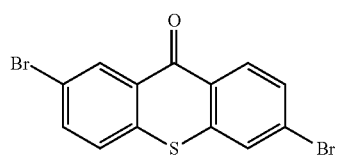 [SMILES: O=c1c2ccc(Br)cc2sc2ccc(Br)cc12]

and hydrogen peroxide.

The specific implementing steps of the step 14 are:

In 250 ml boiling flask-3-neck, 5 g (13.59 mmol), 50 mL dichloromethane

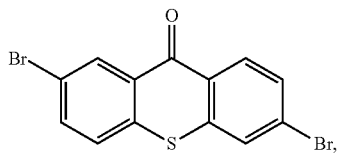 [SMILES: O=c1c2ccc(Br)cc2sc2ccc(Br)cc12]

20 mL ethylic acid, 3 mL (5 equ) hydrogen peroxide are added. The reaction last 8 hours at 80° C., and the temperature is lowered after the reaction is completed, and water is used to remove redundant hydrogen peroxide for extraction.

Through column, 4.6 g intermediate

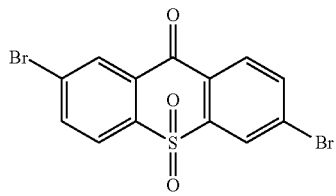

is obtained, and productivity is 85%. Molecular formula: $C_{13}H_6Br_2O_3S$; M/Z=399.84; theoretic value: 402.06; elemental analysis: 401.84 (100.0%), 399.84 (50.0%), 403.84 (48.1%), 402.84 (15.0%), 404.84 (7.8%), 400.84 (7.5%), 403.83 (4.4%), 405.83 (2.2%).

step 2, obtaining light emitting material with Ullmann reaction or Suzuki reaction of the intermediate

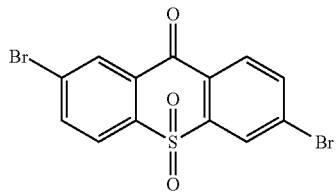

and an aromatic amine compound, in which a constitutional formula of the light emitting material is

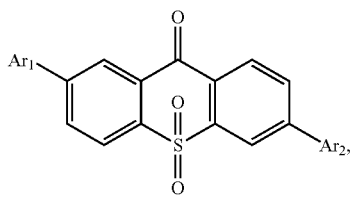

wherein $Ar_1$ and $Ar_2$ are respectively selected from aromatic amine groups shown in formula (1), formula (2), formula (3), formula (4), formula (5), formula (6), formula (7);

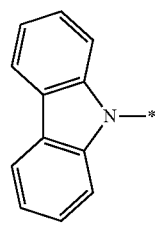
(1)

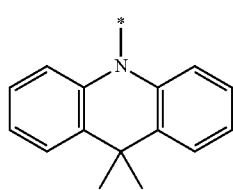
(2)

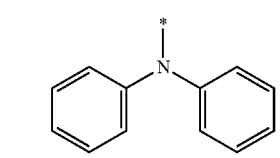
(3)

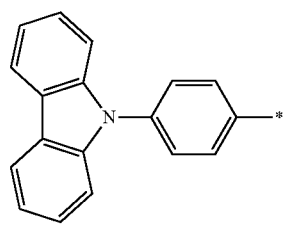
(4)

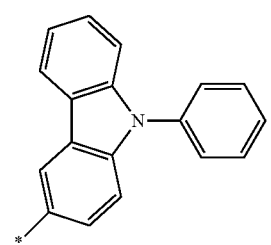
(5)

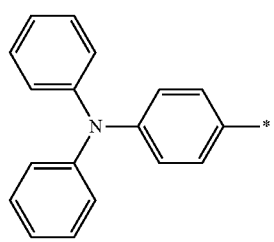
(6)

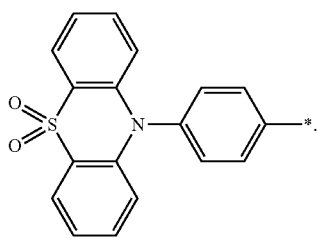
(7)

Preferably, $Ar_1$ and $Ar_2$ are the same.

Specifically, the light emitting material comprises one or more of following compounds:

29 30
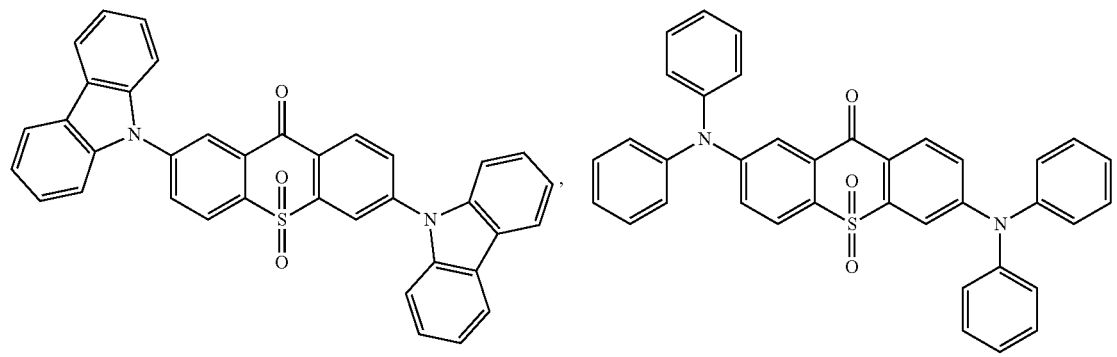
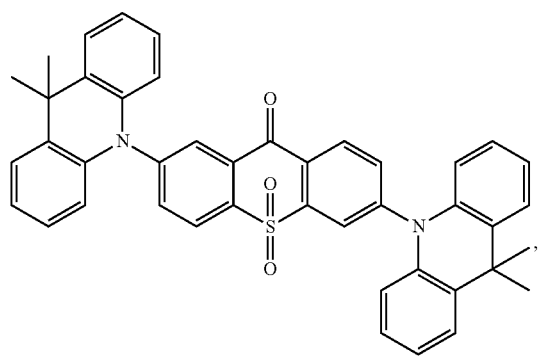
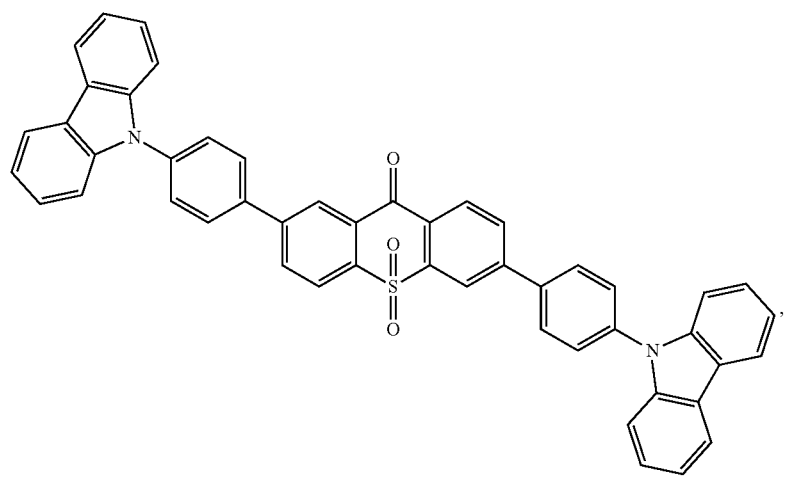
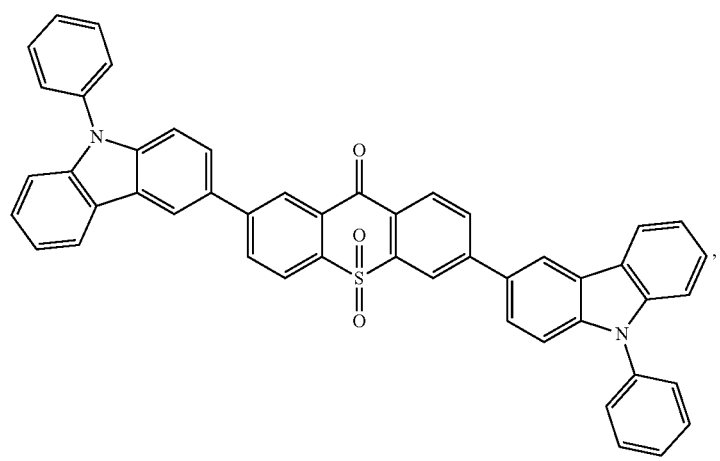

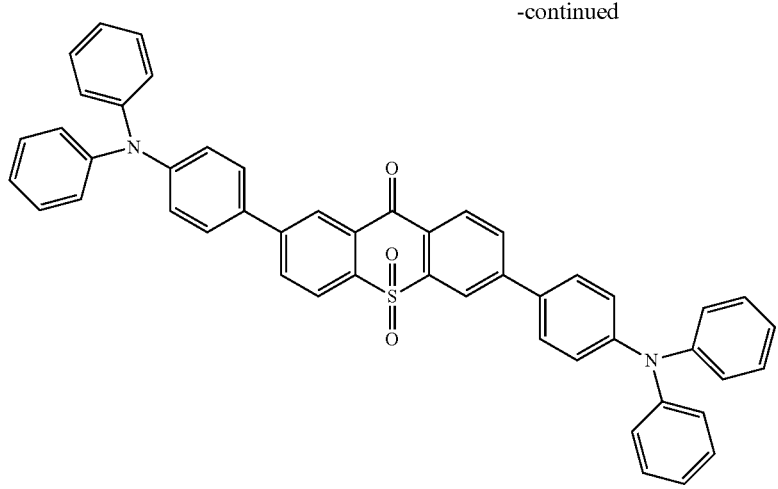

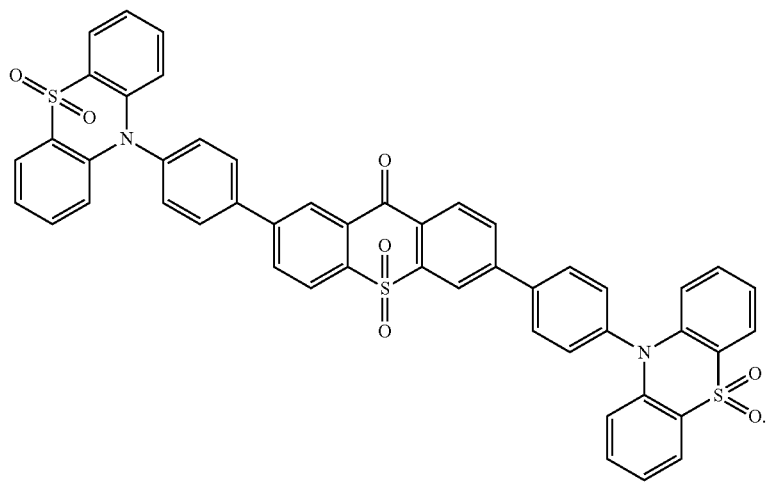

Specifically, in the step 2, the aromatic amine compound comprises one or more of carbazol, diphenylamine, 9,9-diMethylacridan, 4-carbazoleBenzene borate ester, 4-phenylcarbazole borate ester, 4-triphenylamine borate ester, 4-phenylthiophene-S,S-dioxide borate ester;

a constitutional formula of the carbazol is

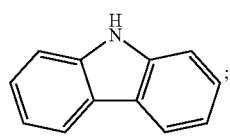 [SMILES: c1ccc2c(c1)[nH]c1ccccc12]

a constitutional formula of the diphenylamine is

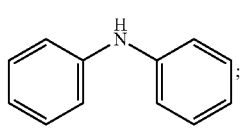 [SMILES: c1ccc(Nc2ccccc2)cc1]

a constitutional formula of the 9,9-diMethylacridan is

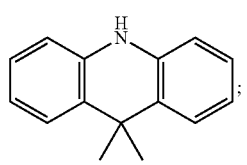 [SMILES: CC1(C)c2ccccc2Nc2ccccc21]

a constitutional formula of the 4-carbazoleBenzene borate ester is

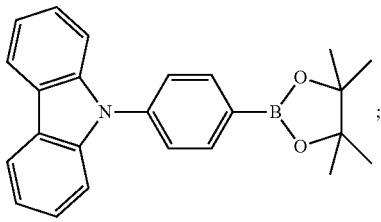 [SMILES: CC1(C)OB(c2ccc(-n3c4ccccc4c4ccccc43)cc2)OC1(C)C]

a constitutional formula of the 4-phenylcarbazole borate ester is

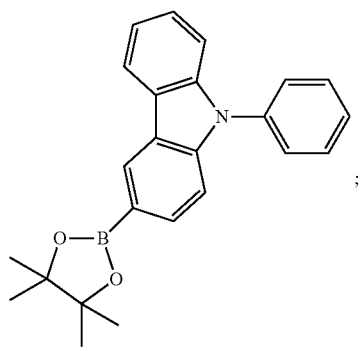 [SMILES: CC1(C)OB(c2ccc3c(c2)c2ccccc2n3-c2ccccc2)OC1(C)C]

a constitutional formula of the 4-triphenylamine borate ester is

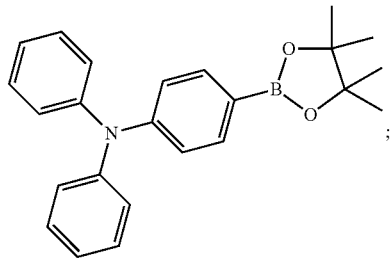 [SMILES: CC1(C)OB(c2ccc(N(c3ccccc3)c3ccccc3)cc2)OC1(C)C]

a constitutional formula of the 4-phenylthiophene-S,S-dioxide borate ester is

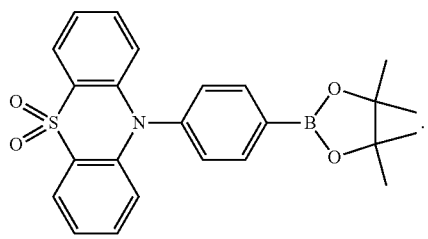 [SMILES: CC1(C)OB(c2ccc(N3c4ccccc4S(=O)(=O)c4ccccc43)cc2)OC1(C)C]

The specific implementing method of the step 2 is described below in detail with combination of the specific embodiment.

Embodiment 1:

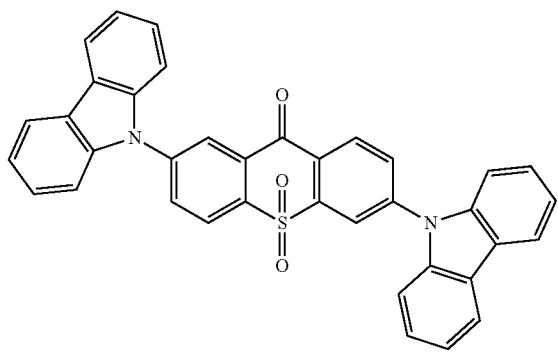

is obtained with Ullmann reaction of intermediate

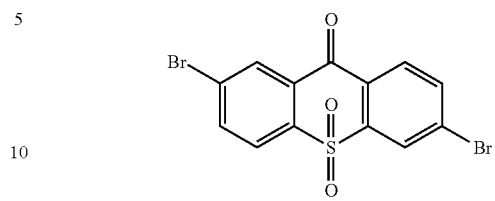

and carbazol, and the reaction formula is:

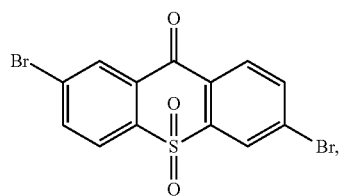

The specific implementing steps are:

Under the protection of nitrogen, in boiling flask-3-neck, 100 ml methylbenzene, 0.72 g (2 mmol) intermediate 0.67 g (4 mmol) carbazol are added, and 0.3 g sodium tert-butoxide is added in stirring, and then 20 mg tris (dibenzylideneacetone)dipalladium (Pd2(dba)3) is added, and then 0.3 ml 10% tri-tert-butylphosphine hexane solution is added, and heated reflux to react overnight. The temperature is lowered, and extracted in dichloromethane in organic phase, and spin dried, and through column. White color solid product 0.81 g is obtained, and productivity is 75%. Molecular formula: $C_{37}H_{22}N_2O_3S$; M/S=574.14; theoretic value: 574.65; elemental analysis: 574.14 (100.0%), 575.14 (40.4%), 576.14 (9.2%), 576.13 (4.5%), 577.13 (1.8%), 575.13 (1.5%), 577.15 (1.0%).

Embodiment 2:

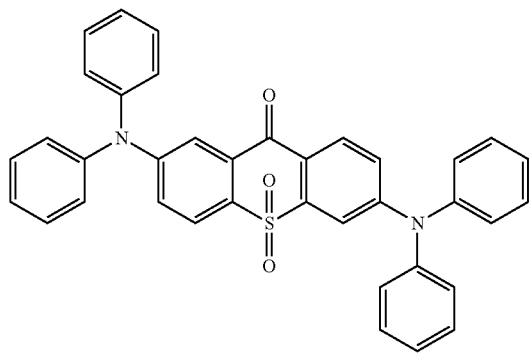

is obtained with Ullmann reaction of intermediate

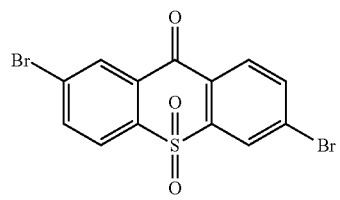

and diphenylamine, and the reaction formula is:

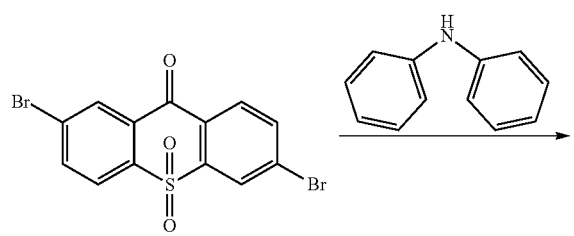

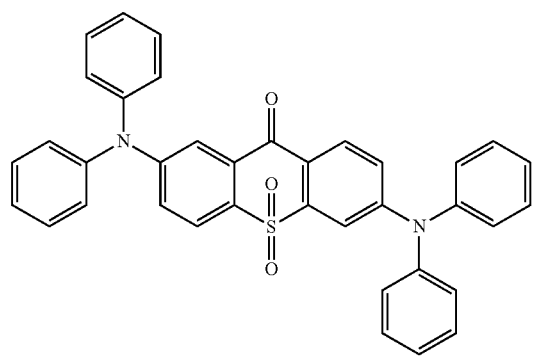

The specific implementing steps are:

Under the protection of nitrogen, in boiling flask-3-neck, 100 ml methylbenzene, 0.72 g (2 mmol) intermediate

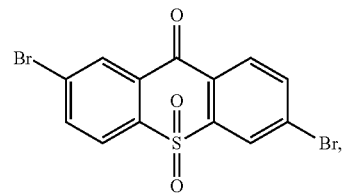

0.84 g (4 mmol) diphenylamine are added, and 0.3 g sodium tert-butoxide is added in stirring, and then 20 mg tris (dibenzylideneacetone)dipalladium (Pd2(dba)3) is added, and then 0.3 ml 10% tri-tert-butylphosphine hexane solution is added, and heated reflux to react overnight. The temperature is lowered, and extracted in dichloromethane in organic phase, and spin dried, and through column. White color solid product 0.81 g is obtained, and productivity is 75%. Molecular formula: $C_{37}H_{26}N_2O_3S$; M/S=578.17; theoretic value: 578.68; elemental analysis: 578.17 (100.0%), 579.17 (41.2%), 580.17 (9.1%), 580.16 (4.5%), 581.17 (2.2%), 581.18 (1.0%).

Embodiment 3:

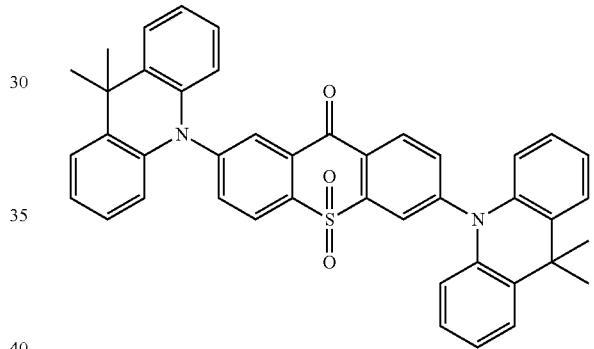

is obtained with Ullmann reaction of intermediate and 9,9-diMethylacridan, and the reaction formula is:

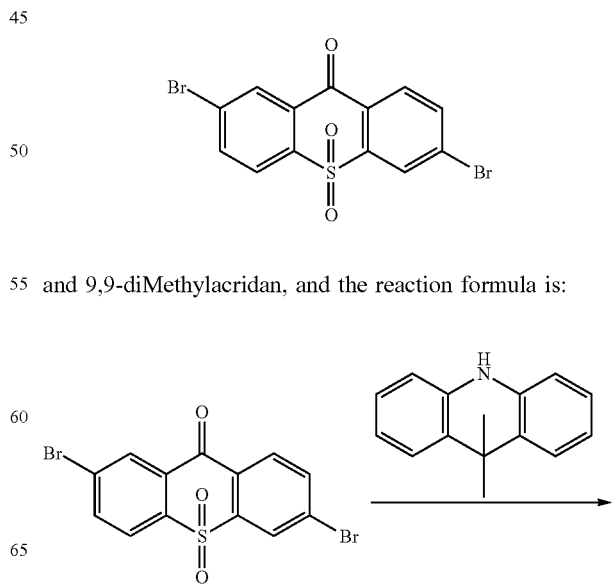

-continued

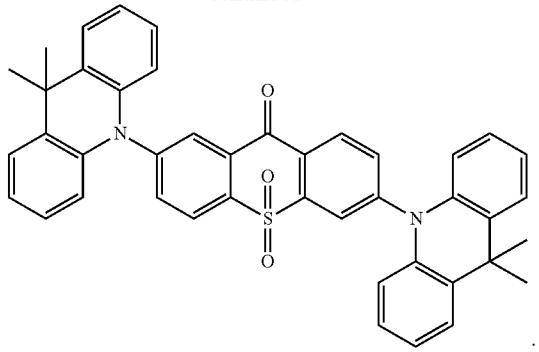

The specific implementing steps are:

Under the protection of nitrogen, in boiling flask-3-neck, 100 ml methylbenzene, 0.72 g (2 mmol) intermediate

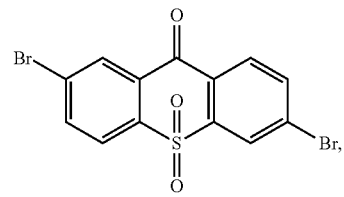

0.84 g (4 mmol) 9,9-diMethylacridan are added, and 0.3 g sodium tert-butoxide is added in stirring, and then 20 mg tris(dibenzylideneacetone)dipalladium (Pd2(dba)3) is added, and then 0.3 ml 10% tri-tert-butylphosphine hexane solution is added, and heated reflux to react overnight. The temperature is lowered, and extracted in dichloromethane in organic phase, and spin dried, and through column. White color solid product 0.85 g is obtained, and productivity is 79%. Molecular formula: $C_{43}H_{34}N_2O_3S$; M/S=658.23; theoretic value: 658.81; elemental analysis: 658.23 (100.0%), 659.23 (48.2%), 660.24 (10.8%), 660.22 (4.5%), 661.23 (2.2%), 661.24 (2.0%), 660.23 (1.3%).

Embodiment 4:

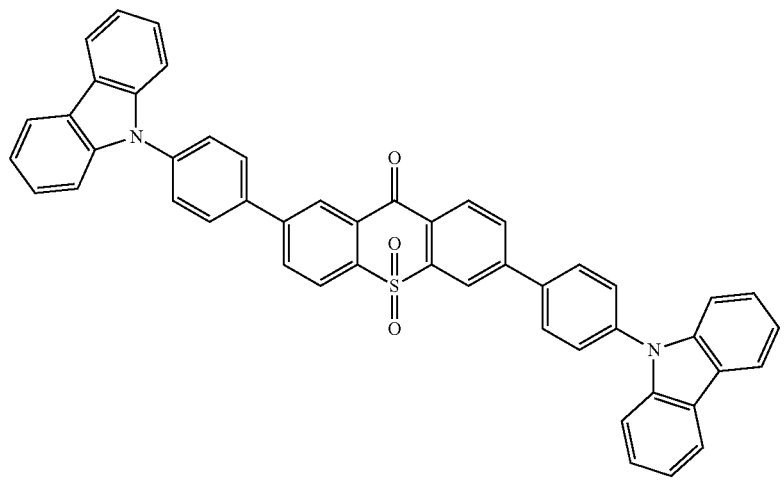

is obtained with Suzuki reaction of intermediate

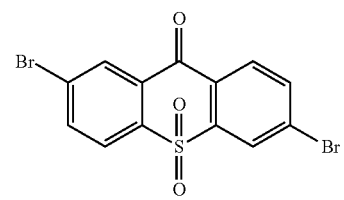

and 4-carbazoleBenzene borate ester, and the reaction formula is:

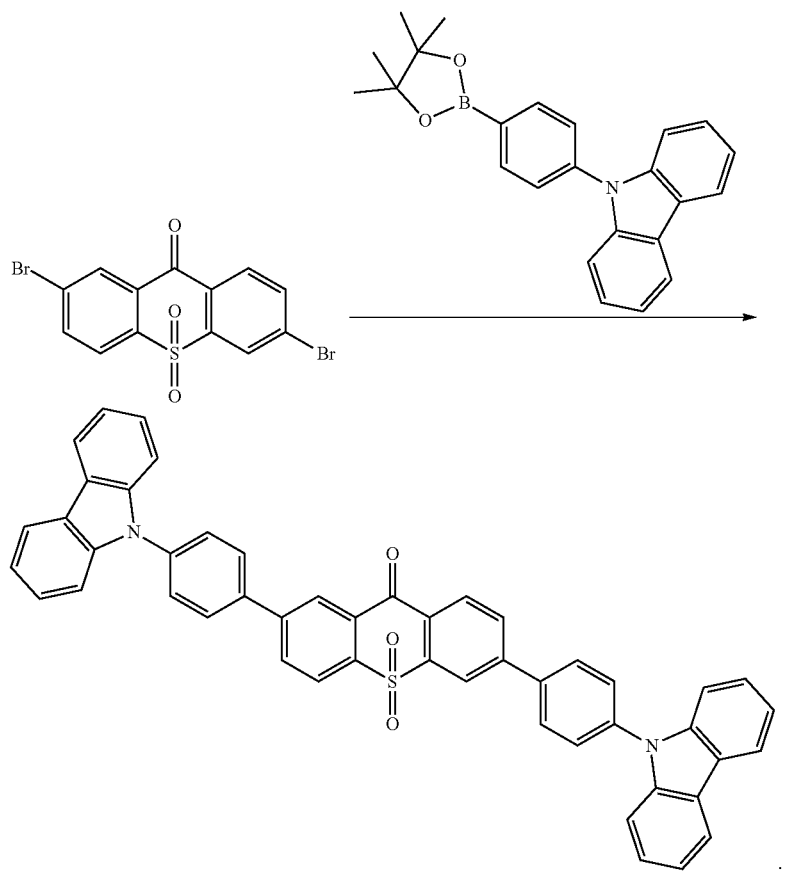

The specific implementing steps are:

Under the atmosphere of nitrogen, in 250 ml boiling flask, 96 ml methylbenzene, 32 ml alcohol, 16 ml 2M potassium carbonate aqueous solution, 0.72 g (2 mmol) intermediate

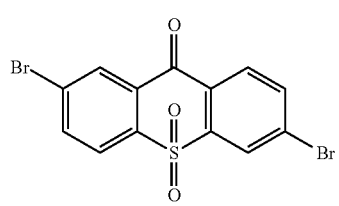

2.06 g (1.2 equ) 4-carbazoleBenzene borate ester are added, and stirred at the room temperature, and then 100 mg triphenylphosphineplatinum (catalyzer) is added and 96° C. reflows for 24 hours. It is cooled to the room temperature, and extracted in dichloromethane, and dried in anhydrous magnesium sulfate. White color solid product 0.86 g is obtained, and productivity is 79%. Molecular formula: $C_{49}H_{30}N_2O_3S$; M/S=726.2; theoretic value: 726.84; elemental analysis: 726.20 (100.0%), 727.20 (54.3%), 728.20 (15.2%), 728.19 (4.5%), 729.21 (2.7%), 729.20 (2.6%).

Embodiment 5:

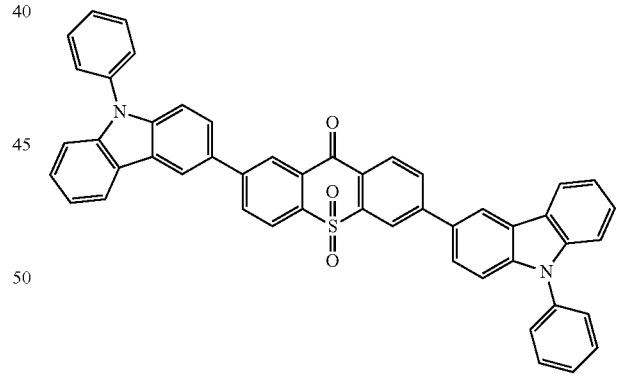

is obtained with Suzuki reaction of intermediate and 4-phenylcarbazole borate ester, and the reaction formula is:

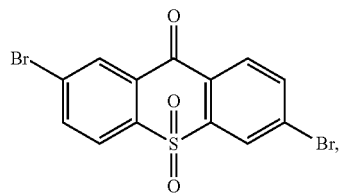

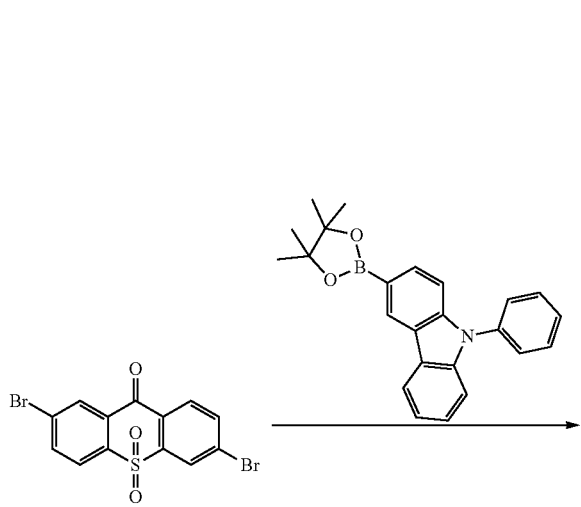

2.32 g (1.2 equ) 4-phenylcarbazole borate ester are added, and stirred at the room temperature, and then 100 mg triphenylphosphineplatinum (catalyzer) is added and 96° C. reflows for 24 hours. It is cooled to the room temperature, and extracted in dichloromethane, and dried in anhydrous magnesium sulfate. White color solid product 0.92 g is obtained, and productivity is 83%. Molecular formula: $C_{49}H_{30}N_2O_3S$; M/S=726.2; theoretic value: 726.84; elemental analysis: 726.20 (100.0%), 727.20 (54.3%), 728.20 (15.2%), 728.19 (4.5%), 729.21 (2.7%), 729.20 (2.6%).

Embodiment 6:

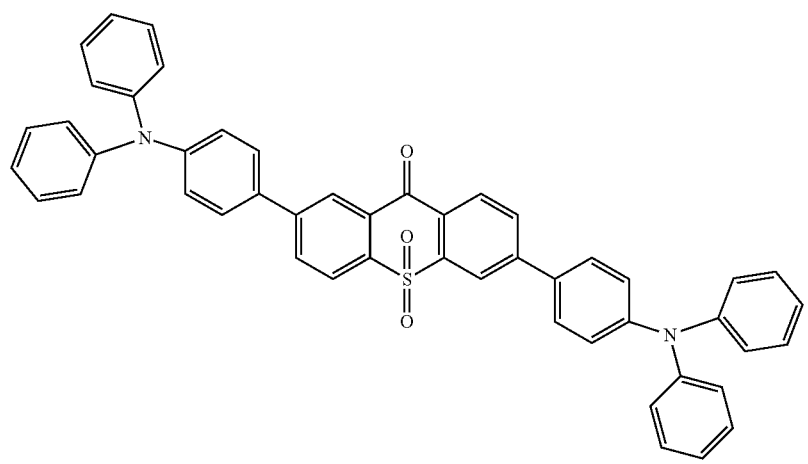

is obtained with Suzuki reaction of intermediate

-continued

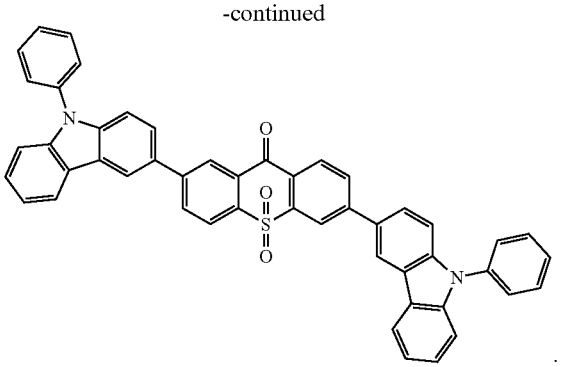

and 4-triphenylamine borate ester, and the reaction formula is:

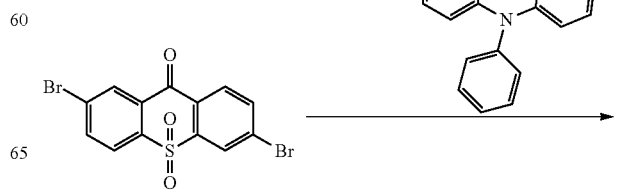

The specific implementing steps are:

Under the atmosphere of nitrogen, in 250 ml boiling flask, 96 ml methylbenzene, 32 ml alcohol, 16 ml 2M potassium carbonate aqueous solution, 0.72 g (2 mmol) intermediate -continued

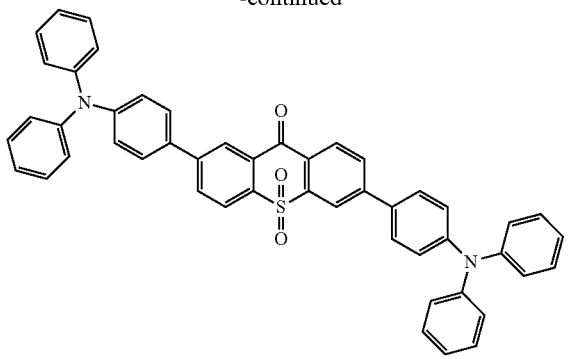

The specific implementing steps are:
Under the atmosphere of nitrogen, in 250 ml boiling flask, 96 ml methylbenzene, 32 ml alcohol, 16 ml 2M potassium carbonate aqueous solution, 0.72 g (2 mmol) intermediate

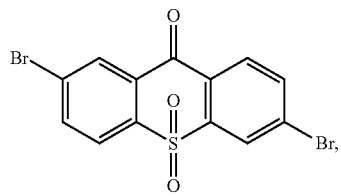

2.32 g (1.2 equ) 4-triphenylamine borate ester are added, and stirred at the room temperature, and then 100 mg triphenylphosphineplatinum (catalyzer) is added and 96° C. reflows for 24 hours. It is cooled to the room temperature, and extracted in dichloromethane, and dried in anhydrous magnesium sulfate. White color solid product 0.96 g is obtained, and productivity is 87%. Molecular formula: $C_{49}H_{34}N_2O_3S$; M/S=730.23; theoretic value: 730.87; elemental analysis: 730.23 (100.0%), 731.23 (54.7%), 732.24 (14.0%), 732.22 (4.5%), 733.24 (2.8%), 733.23 (2.5%), 732.23 (1.4%).

Embodiment 7:

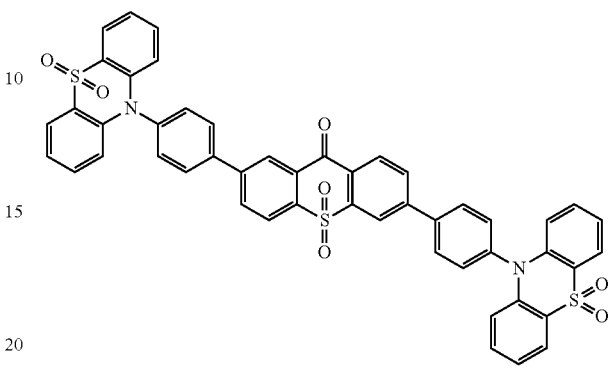

is obtained with Suzuki reaction of intermediate and 4-phenylthiophene-S,S-dioxide borate ester, and the reaction formula is:

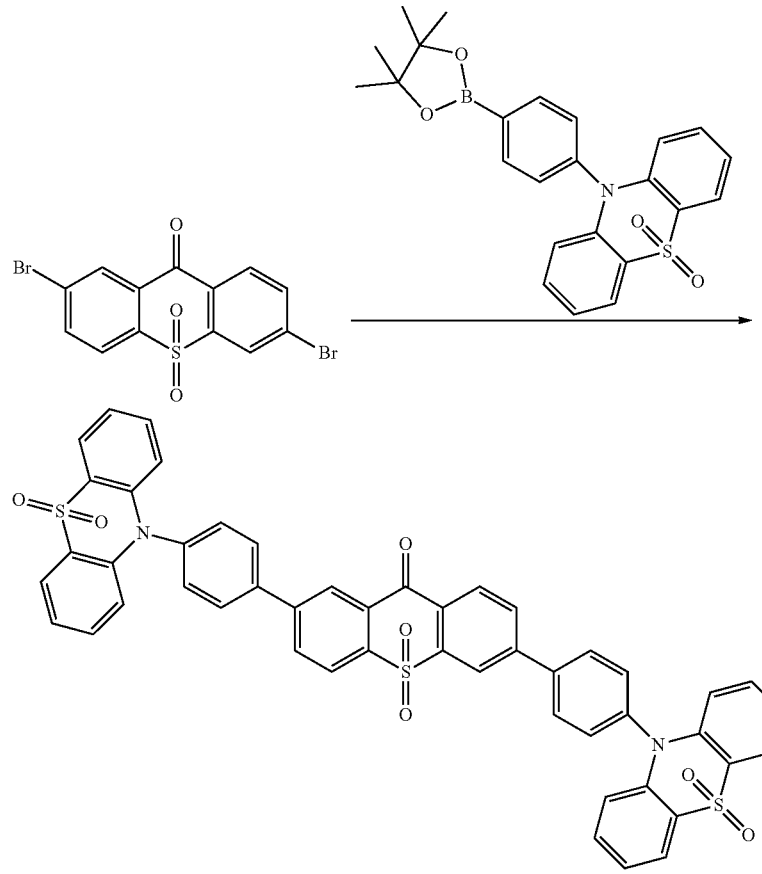

The specific implementing steps are:

Under the atmosphere of nitrogen, in 250 ml boiling flask, 96 ml methylbenzene, 32 ml alcohol, 16 ml 2M potassium carbonate aqueous solution, 0.72 g (2 mmol) intermediate

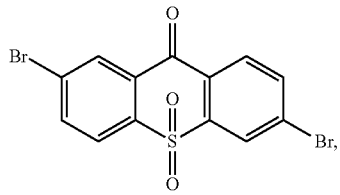

2.06 g (1.2 equ) 4-phenylthiophene-S,S-dioxide borate ester are added, and stirred at the room temperature, and then 100 mg triphenylphosphineplatinum (catalyzer) is added and 96° C. reflows for 24 hours. It is cooled to the room temperature, and extracted in dichloromethane, and dried in anhydrous magnesium sulfate. White color solid product 0.96 g is obtained, and productivity is 87%. Molecular formula: $C_{49}H_{30}N_2O_7S_3$; M/S=854.12; theoretic value: 854.97; elemental analysis: 854.12 (100.0%), 855.12 (56.1%), 856.13 (15.5%), 856.12 (15.3%), 857.12 (7.5%), 857.13 (3.7%), 858.12 (2.3%).

In the aforesaid manufacture method of the light emitting material, p-bromothiophenol and 4-Bromo-2-fluorobenzonitrile are employed to be starting materials, and the intermediate of the light emitting material is obtained with a series of simple reactions, and finally, the light emitting material is obtained with Ullmann reaction or Suzuki reaction, and the steps are simple and the production is high.

Figure 2:
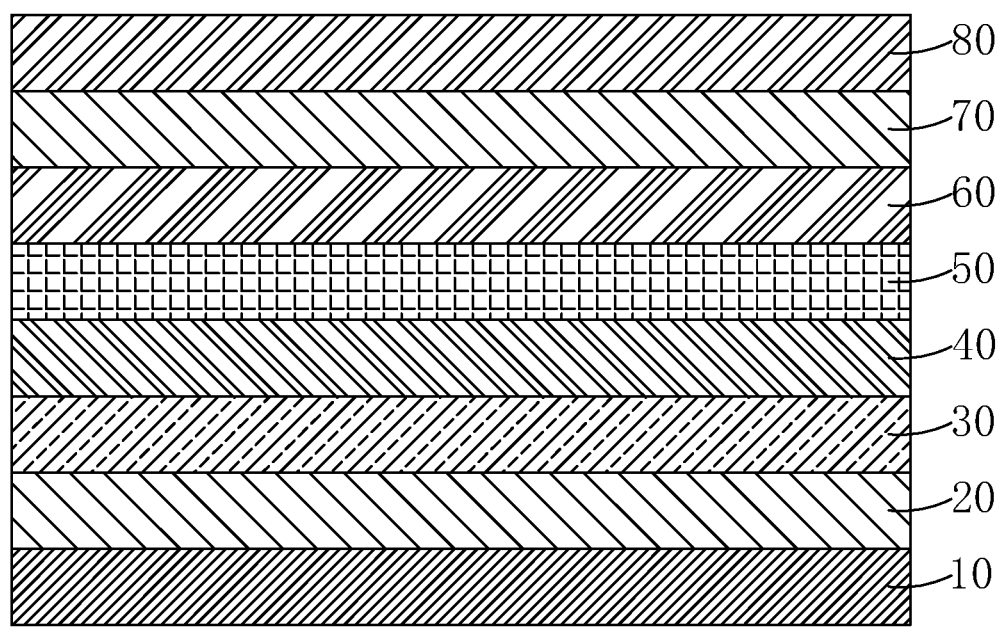
FIG. 2 is a structure diagram of an organic light emitting diode according to the present invention.

Please refer to FIG. 2. The present invention further provides an organic light emitting diode, comprising a substrate 10, and an anode 20, a Hole Injection Layer 30, a Hole Transporting Layer 40, a light emitting layer 50, an Electron Transport Layer 60, an Electron Injection Layer 70 and a cathode 80 stacking up on the substrate 10 from bottom to top in order;

the light emitting layer 50 comprises light emitting material, in which a constitutional formula is

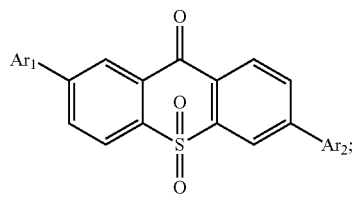

wherein $Ar_1$ and $Ar_2$ are respectively selected from aromatic amine groups shown in formula (1), formula (2), formula (3), formula (4), formula (5), formula (6), formula (7);

(1)

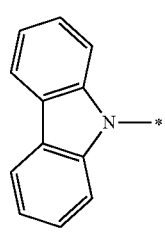

(2)

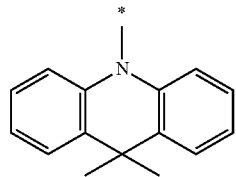

(3)

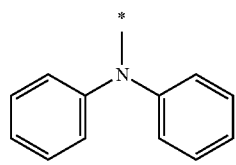

(4)

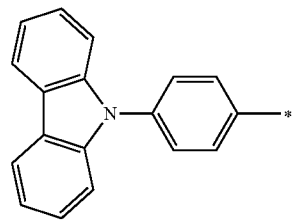

(5)

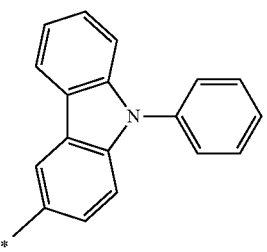

(6)

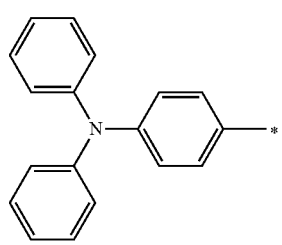

(7)

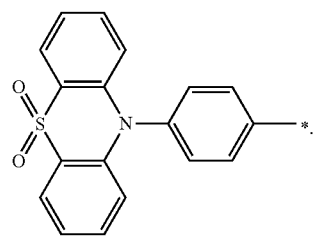

Preferably, $Ar_1$ and $Ar_2$ are the same.

Specifically, the light emitting material comprises one or more of following compounds:

47 48
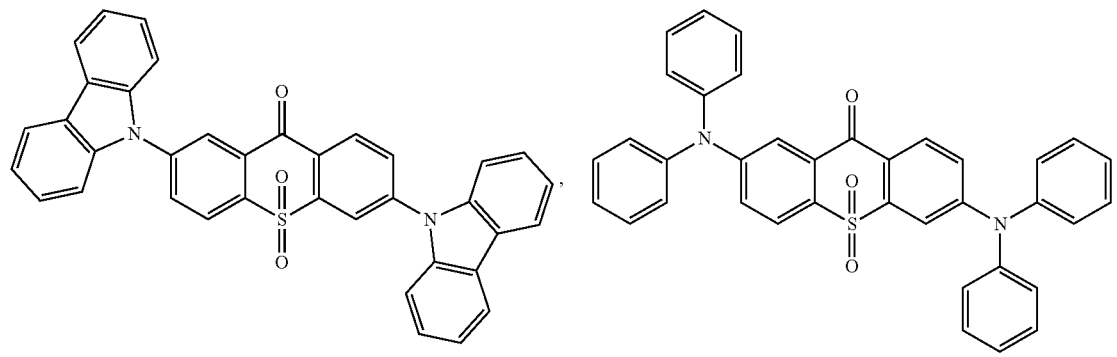
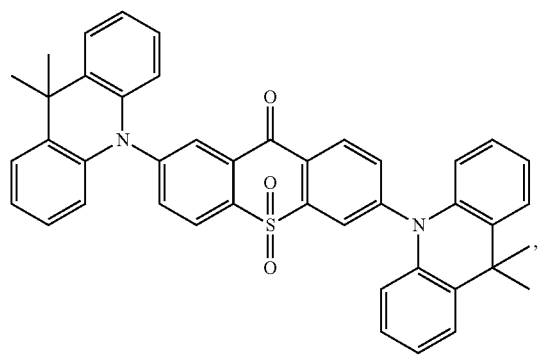
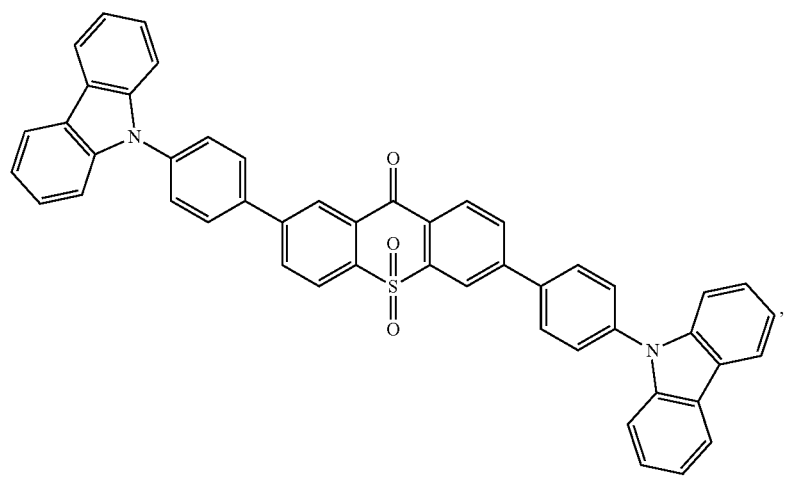
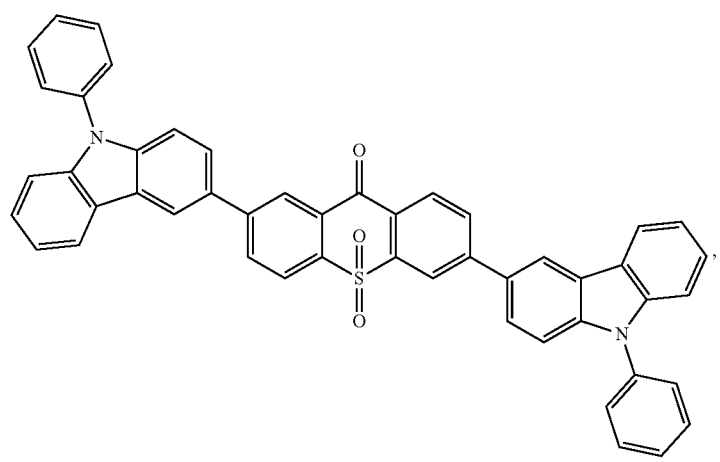

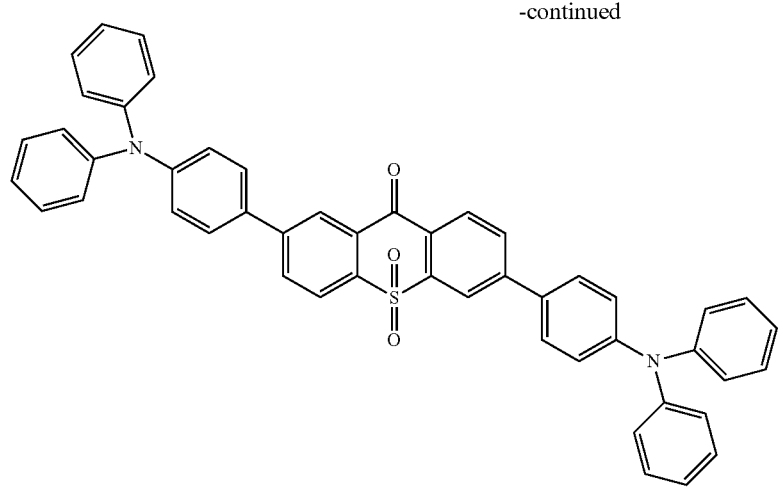

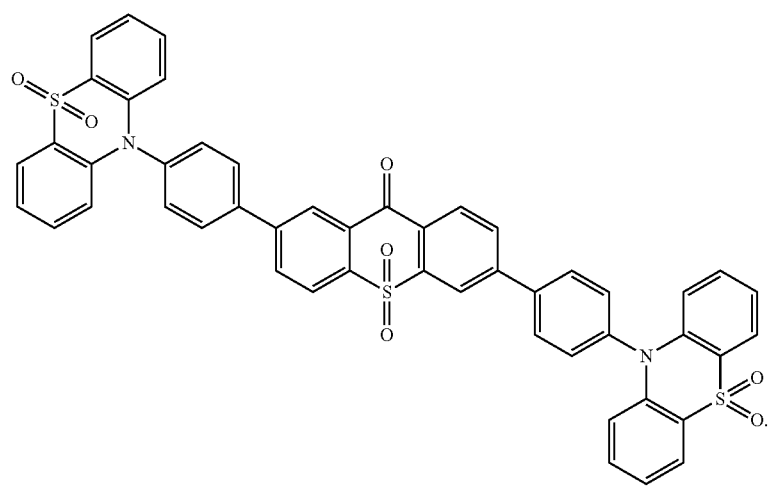

Preferably, in material of the light emitting layer 50, a mass percentage of the light emitting material is 1%.

Specifically, the light emitting layer 50 can emit red light, yellow light, green light or blue light.

Specifically, material of the anode 20 comprises transparent metal oxide. The transparent metal oxide is preferably to be Indium Tin Oxide (ITO).

Specifically, material of the Hole Injection Layer 30 comprises 2,3,6,7,10,11-Hexacyano-1,4,5,8,9,12-hexaazatriphenylene (HAT-CN), and a constitutional formula of the 2,3,6,7,10,11-Hexacyano-1,4,5,8,9,12-hexaazatriphenylene is.

Specifically, material of the Hole Transporting Layer 40 comprises 1,1-Bis[4-[N,N-di(p-tolyl)amino]phenyl]cyclohexane (TAPC), and a constitutional formula of the 1,1-Bis[4-[N,N-di(p-tolyl)amino]phenyl]cyclohexane is

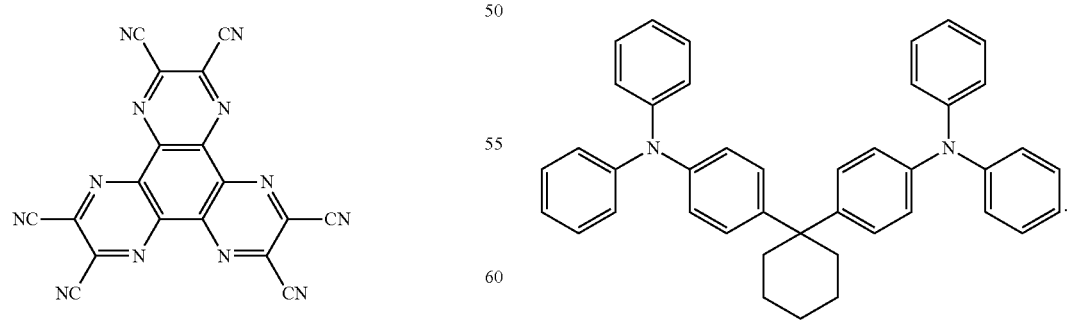

Specifically, material of the light emitting layer 50 further comprises 4,4'-Bis(N-carbazolyl)-1,1'-biphenyl (CBP), and a constitutional formula of the 4,4'-Bis(N-carbazolyl)-1,1'-biphenyl is

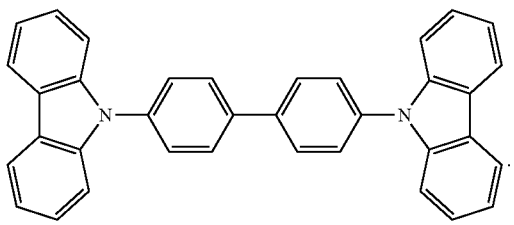 [SMILES: c1ccc2c(c1)c1ccccc1n2-c1ccc(-c2ccc(-n3c4ccccc4c4ccccc43)cc2)cc1]

Specifically, material of the Electron Transport Layer 60 comprises 1,3,5-tri[(3-pyridyl)-phen-3-yl]benzene (TmPyPB), and a constitutional formula of the 1,3,5-tri[(3-pyridyl)-phen-3-yl]benzene is

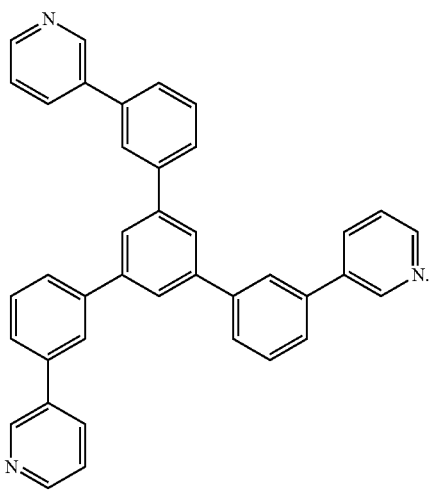 [SMILES: c1cncc(-c2cccc(-c3cc(-c4cccc(-c5cccnc5)c4)cc(-c4cccc(-c5cccnc5)c4)c3)c2)c1]

Specifically, material of the Electron Injection Layer 70 comprises Lithium fluoride (LiF).

Specifically, material of cathode 80 comprises aluminum (Al).

Preferably, a thickness of the anode 20 is 95 mm, and a thickness of the Hole Injection Layer 30 is 5 mm, and a thickness of the Hole Transporting Layer 40 is 20 mm, and a thickness of the light emitting layer 50 is 35 mm, and a thickness of the Electron Transport Layer 60 is 55 mm, and a thickness of the Electron Injection Layer 70 is 1 mm, and a thickness of the cathode 80 is larger than 80 nm.

The manufacture process of the organic light emitting diode is: putting Indium Tin Oxide transparent conductive glass in the cleaner for the ultrasonic process, and using the deionized water for cleaning to employ ultrasound to remove oil in the mixture solution of acetone/ethanol, and then, baking the same in the clean environment until the water is completely removed, and then, using ultraviolet light and ozone for cleaning, and employing low energy cation to bombard the same to obtain the anode 20, and putting the transparent conductive glass with the anode 20 in the vacuum chamber, and vacuuming to $1\times10^{-5}$-$9\times10^{-3}$ Pa, and next, sequentially evaporating the Hole Injection Layer 30, the Hole Transporting Layer 40, the plurality of light emitting layer 50, the Electron Transport Layer 60, the Electron Injection Layer 70 and the cathode 80 on the anode 20, and ultimately obtaining the organic light emitting diode of this embodiment.

In conclusion, the present invention provides a light emitting material, in which the structure is unitary, and the formula weight is determined, and the better solubility and film formation are provided, and the thin film status is stable; it possesses a very high decomposition temperature and a lower sublimation temperature, and is easy to sublime to be light emitting material of high purity, and can be applied for small molecule organic light emitting diode; by changing the aromatic amine group, which is connected, the physical property can be improved in advance to promote the performance of the photoelectric element of the light emitting material. The present invention provides a manufacture method of the light emitting material. p-bromothiophenol and 4-Bromo-2-fluorobenzonitrile are employed to be starting materials, and the intermediate of the light emitting material is obtained with a series of simple reactions, and finally, the light emitting material is obtained with Ullmann reaction or Suzuki reaction, and the steps are simple and the production is high. The present invention provides an organic light emitting diode, in which the light emitting layer comprises the aforesaid light emitting material that has higher light emission efficiency and stability.

Above are only specific embodiments of the present invention, the scope of the present invention is not limited to this, and to any persons who are skilled in the art, change or replacement which is easily derived should be covered by the protected scope of the invention. Thus, the protected scope of the invention should go by the subject claims.

What is claimed is:

1. A light emitting material of the following constitutional formula:

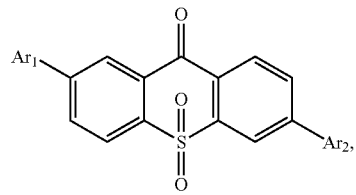

wherein $Ar_1$ and $Ar_2$ are respectively selected from aromatic amine groups shown in formula (1), formula (2), formula (3), formula (4), formula (5), formula (6), formula (7);

(1)

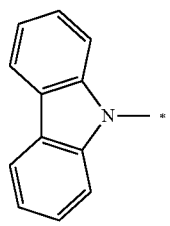

(2)

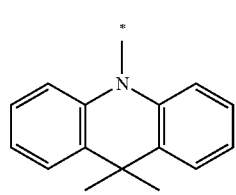

-continued
(3)
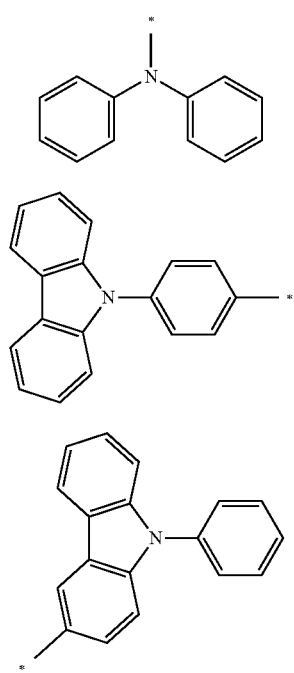
(4)
(5)
-continued
(6)
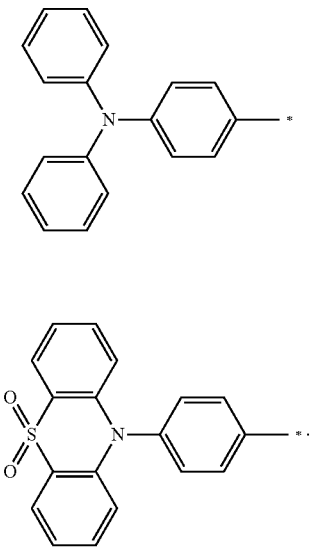
(7)
2. The light emitting material according to claim 1, wherein $Ar_1$ and $Ar_2$ are the same.
3. The light emitting material according to claim 2, selected from one of the following compounds:
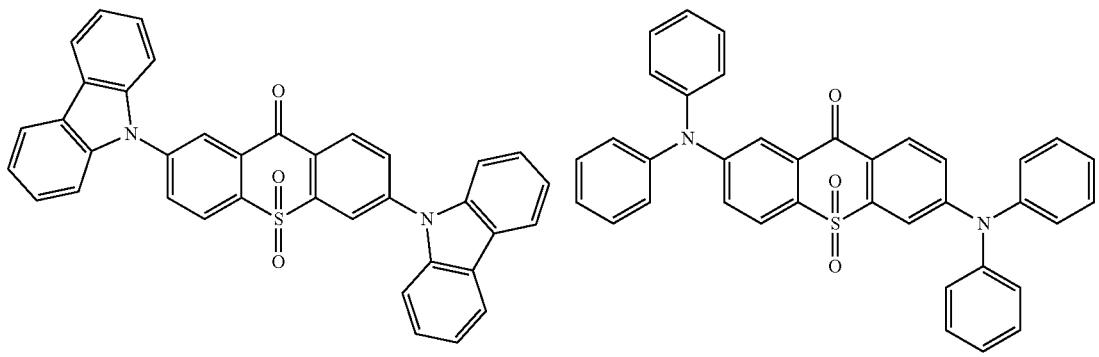
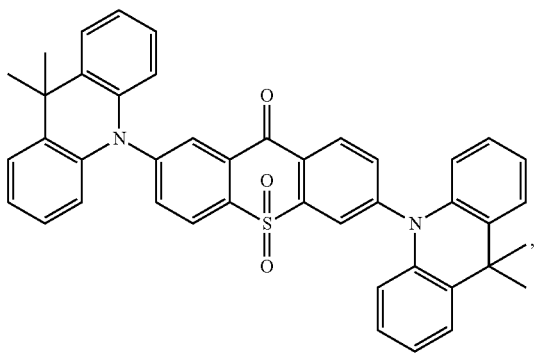

-continued
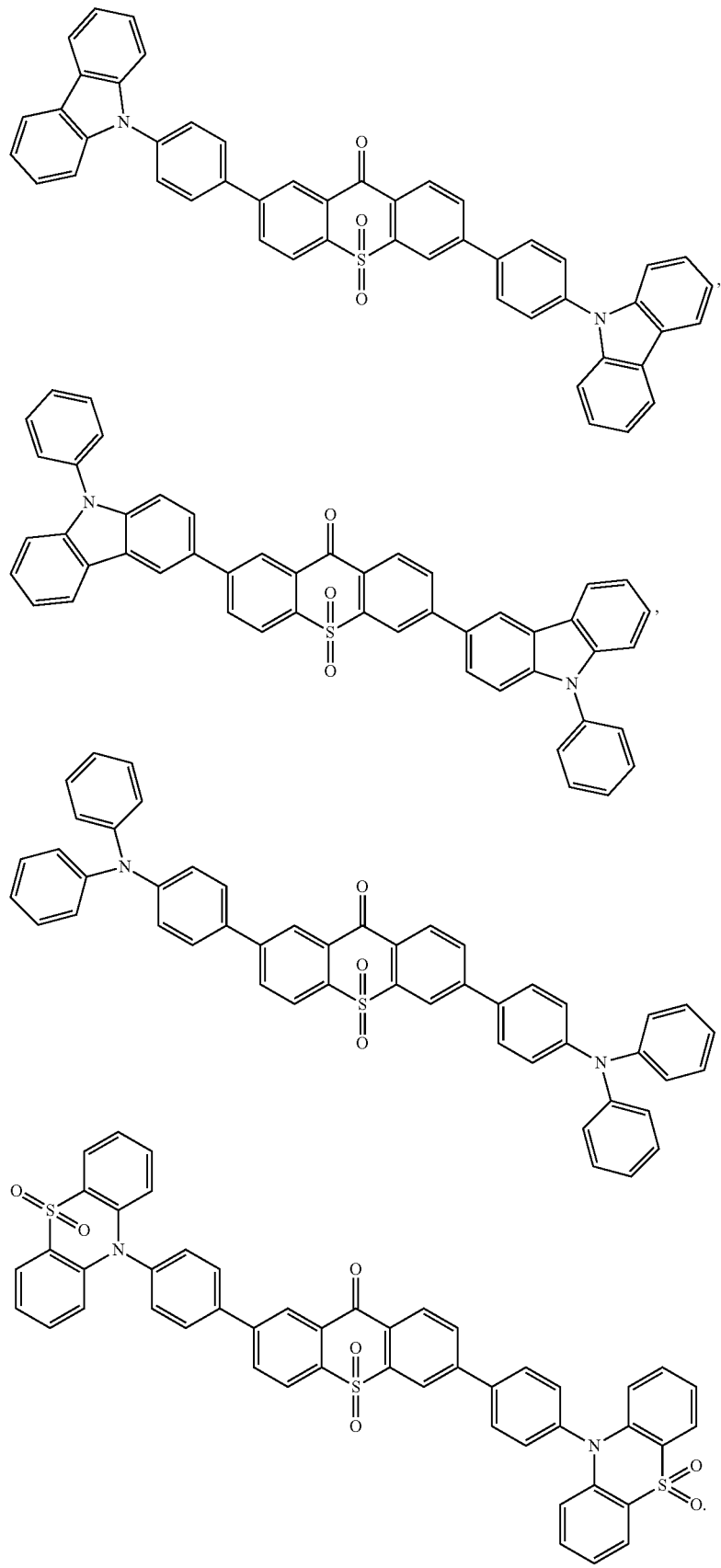

4. An organic light emitting diode, comprising a substrate, and an anode, a hole injection layer, a hole transporting layer, a light emitting layer, an electron transport layer, an electron injection layer and a cathode stacking up on the substrate from bottom to top in order;

the light emitting layer comprises a light emitting material of the following constitutional formula

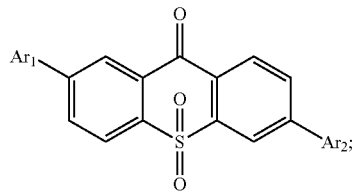

wherein $Ar_1$ and $Ar_2$ are respectively selected from aromatic amine groups shown in formula (1), formula (2), formula (3), formula (4), formula (5), formula (6), formula (7);

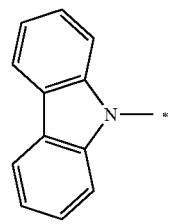
(1)

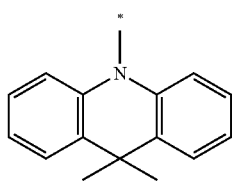
(2)

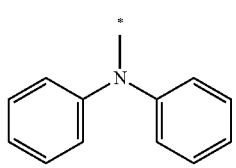
(3)

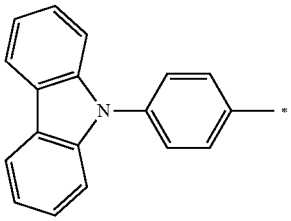
(4)

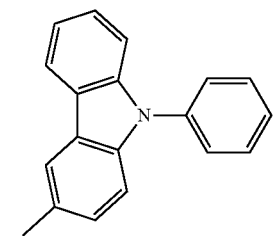
(5)

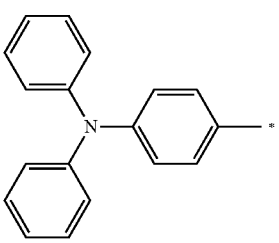
(6)

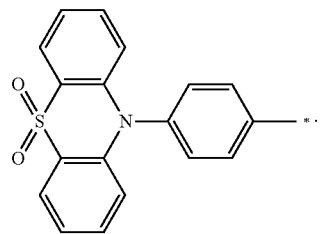
(7)

5. The organic light emitting diode according to claim 4, wherein $Ar_1$ and $Ar_2$ are the same.

6. The organic light emitting diode according to claim 5, wherein the light emitting material comprises one or more of following compounds:

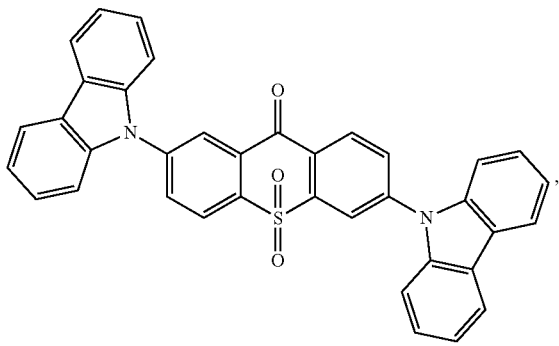
,
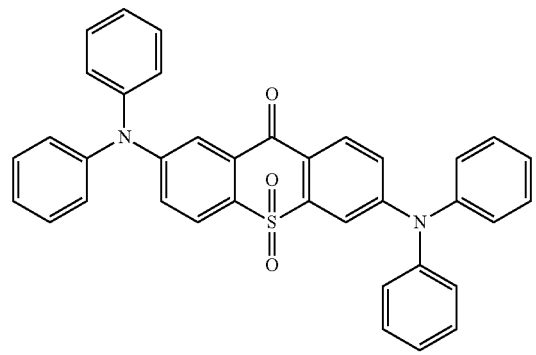

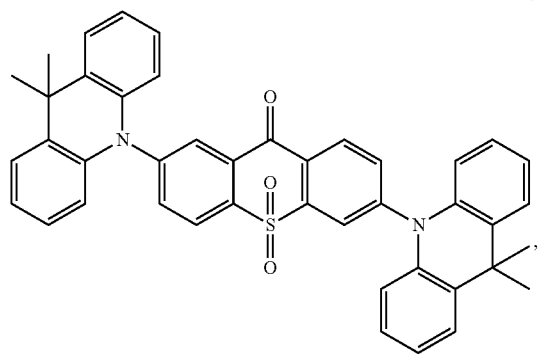
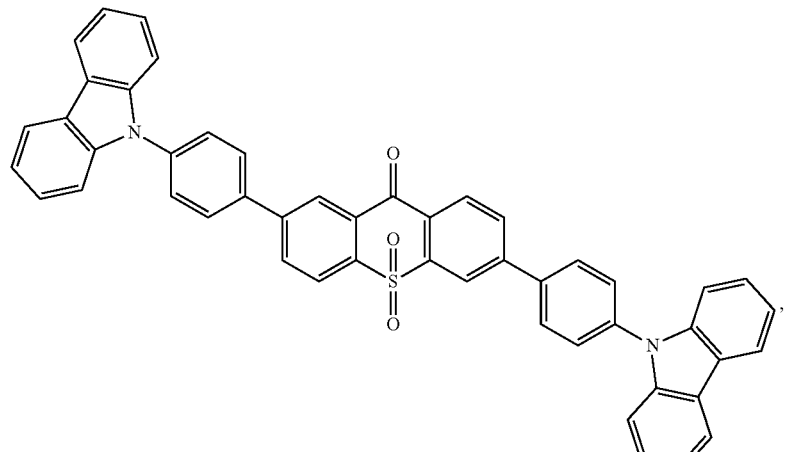
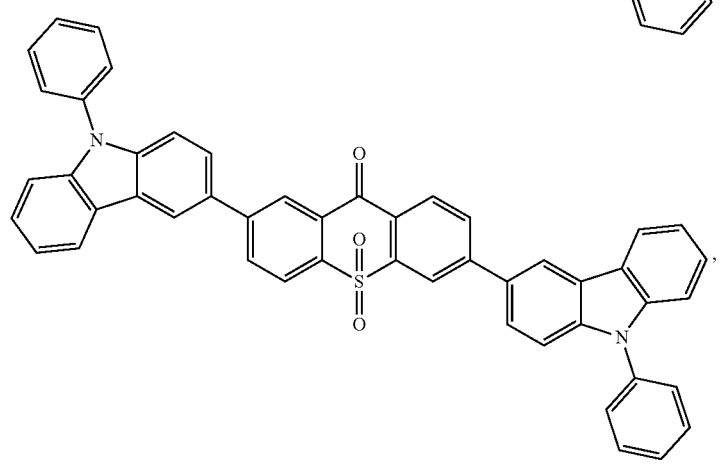
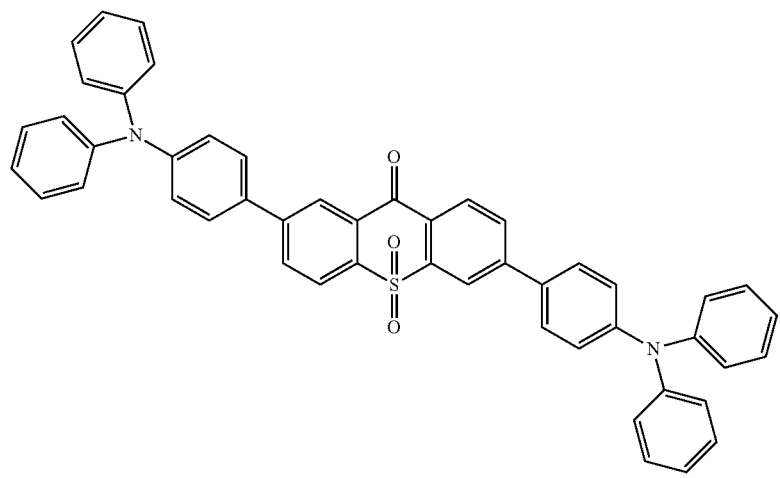

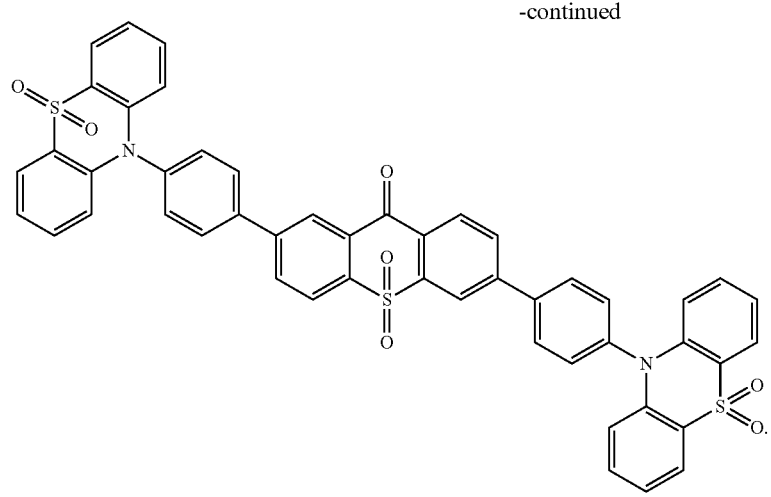
* * * * *